US009826991B2

(12) United States Patent
Kaiser et al.

(10) Patent No.: US 9,826,991 B2
(45) Date of Patent: Nov. 28, 2017

(54) METHOD AND APPARATUS FOR RECONSTRUCTING A HIP JOINT, INCLUDING THE PROVISION AND USE OF A NOVEL ARTHROSCOPIC DEBRIDEMENT TEMPLATE FOR ASSISTING IN THE TREATMENT OF CAM-TYPE FEMOROACETABULAR IMPINGEMENT

(71) Applicant: Pivot Medical, Inc., Sunnyvale, CA (US)

(72) Inventors: William Kaiser, Campbell, CA (US); James Flom, San Carlos, CA (US); Julian Nikolchev, Portola Valley, CA (US); Jeremy Graul, Elk Grove, CA (US)

(73) Assignee: Pivot Medical, Inc., Sunnyvale, CA (US)

( * ) Notice: Subject to any disclaimer, the term of this patent is extended or adjusted under 35 U.S.C. 154(b) by 470 days.

(21) Appl. No.: 14/213,715

(22) Filed: Mar. 14, 2014

(65) Prior Publication Data

US 2014/0316417 A1  Oct. 23, 2014

Related U.S. Application Data

(60) Provisional application No. 61/782,827, filed on Mar. 14, 2013.

(51) Int. Cl.
*A61B 17/17* (2006.01)
*A61B 90/35* (2016.01)
(Continued)

(52) U.S. Cl.
CPC .......... *A61B 17/1742* (2013.01); *A61B 17/15* (2013.01); *A61B 17/154* (2013.01); *A61B 17/155* (2013.01); *A61B 17/157* (2013.01); *A61B 17/158* (2013.01); *A61B 17/16* (2013.01); *A61B 17/1613* (2013.01); *A61B 17/1615* (2013.01); *A61B 17/1668* (2013.01); *A61B 17/17* (2013.01); *A61B 17/1703* (2013.01); *A61B 90/35* (2016.02); *A61B 90/30* (2016.02); *A61B 2017/1602* (2013.01)

(58) Field of Classification Search
CPC ..... A61B 17/15; A61B 17/154; A61B 17/155; A61B 17/157; A61B 17/158; A61B 17/16; A61B 2017/1602; A61B 17/1613; A61B 17/1615; A61B 17/1668; A61B 17/17; A61B 17/1703; A61B 17/1742
See application file for complete search history.

(56) References Cited

U.S. PATENT DOCUMENTS 6,607,561 B2 *  8/2003  Brannon ............ A61B 1/00135
                                                        606/65
7,799,077 B2    9/2010  Lang et al.
(Continued)

*Primary Examiner* — Larry E Waggle, Jr.
(74) *Attorney, Agent, or Firm* — Pandiscio & Pandiscio

(57) ABSTRACT

Apparatus for use in debriding a bone, said apparatus comprising:
an arthroscopic debridement template comprising a body reconfigurable between (i) a first configuration having a first profile and comprising an arc matching the desired curvature of the bone after debridement, and (ii) a second configuration having a second profile, wherein said second profile is smaller than said first profile.

10 Claims, 49 Drawing Sheets

(51) Int. Cl.
*A61B 17/15* (2006.01)
*A61B 17/16* (2006.01)
*A61B 90/30* (2016.01)

(56) References Cited

U.S. PATENT DOCUMENTS

| | | | |
|---|---|---|---|
| 8,057,477 B2 * | 11/2011 | Desarzens | A61B 17/1666 606/80 |
| 8,192,453 B2 * | 6/2012 | Valla | A61B 17/1666 606/180 |
| 2006/0100632 A1 † | 5/2006 | Fell | |
| 2007/0179340 A1 † | 8/2007 | Jorgensen | |
| 2008/0161679 A1 | 7/2008 | von Jako et al. | |
| 2011/0190774 A1 † | 8/2011 | Nikolchev | |
| 2011/0319745 A1 | 12/2011 | Frey | |
| 2012/0004662 A1 † | 1/2012 | Torrie | |
| 2012/0004691 A1 † | 1/2012 | Torrie | |
| 2012/0046526 A1 † | 2/2012 | Boettner | |
| 2013/0211408 A1 † | 8/2013 | Kather | |

\* cited by examiner
† cited by third party

CAM-TYPE FEMOROACETABULAR IMPINGEMENT (FAI)

CAM INJURY TO THE LABRUM

PINCER-TYPE FEMOROACETABULAR IMPINGEMENT (FAI)

PINCER INJURY TO THE LABRUM

METHOD AND APPARATUS FOR RECONSTRUCTING A HIP JOINT, INCLUDING THE PROVISION AND USE OF A NOVEL ARTHROSCOPIC DEBRIDEMENT TEMPLATE FOR ASSISTING IN THE TREATMENT OF CAM-TYPE FEMOROACETABULAR IMPINGEMENT

REFERENCE TO PENDING PRIOR PATENT APPLICATION

This patent application claims benefit of pending prior U.S. Provisional Patent Application Ser. No. 61/782,827, filed Mar. 14, 2013 by Julian Nikolchev et al. for METHOD AND APPARATUS FOR RECONSTRUCTING A HIP JOINT, INCLUDING THE PROVISION AND USE OF A NOVEL INTRAJOINT ARTHROSCOPIC DEBRIDEMENT TEMPLATE FOR ASSISTING IN THE TREATMENT OF CAM-TYPE FEMOROACETABULAR IMPINGEMENT (FAI), which patent application is hereby incorporated herein by reference.

FIELD OF THE INVENTION

This invention relates to surgical methods and apparatus in general, and more particularly to surgical methods and apparatus for reconstructing a hip joint.

BACKGROUND OF THE INVENTION

The hip joint movably connects the leg to the torso. The hip joint is a ball-and-socket joint, and is capable of a wide range of different motions, e.g., flexion and extension, abduction and adduction, medial and lateral rotation, etc. See FIG. 1. With the possible exception of the shoulder joint, the hip joint is perhaps the most mobile joint in the body. Significantly, and unlike the shoulder joint, the hip joint carries substantial weight loads during most of the day, in both static (e.g., standing and sitting) and dynamic (e.g., walking and running) conditions.

The hip joint is susceptible to a number of different pathologies. These pathologies can have both congenital and injury-related origins. In some cases, the pathology can be substantial at the outset. In other cases, the pathology may be minor at the outset but, if left untreated, may worsen over time. More particularly, in many cases an existing pathology may be exacerbated by the dynamic nature of the hip joint and the substantial weight loads imposed on the hip joint.

The pathology may, either initially or thereafter, significantly interfere with patient comfort and lifestyle. In some cases the pathology can be so severe as to require partial or total hip replacement. A number of procedures have been developed for treating hip pathologies short of partial or total hip replacement, but these procedures are generally limited in scope due to the significant difficulties associated with treating the hip joint.

A better understanding of various hip joint pathologies, and also the current limitations associated with their treatment, can be gained from a more precise understanding of the anatomy of the hip joint.

Anatomy of the Hip Joint

The hip joint is formed at the junction of the femur and the hip. More particularly, and looking now at FIG. 2, the ball of the femur is received in the acetabular cup of the hip, with a plurality of ligaments and other soft tissue serving to hold the bones in articulating condition.

More particularly, and looking now at FIG. 3, the femur is generally characterized by an elongated body terminating, at its top end, in an angled neck which supports a hemispherical head (also sometimes referred to as the ball). As seen in FIGS. 3 and 4, a large projection known as the greater trochanter protrudes laterally and posteriorly from the elongated body adjacent to the neck. A second, somewhat smaller projection known as the lesser trochanter protrudes medially and posteriorly from the elongated body adjacent to the neck. An intertrochanteric crest (FIGS. 3 and 4) extends along the periphery of the femur, between the greater trochanter and the lesser trochanter.

Looking next at FIG. 5, the hip is made up of three constituent bones: the ilium, the ischium and the *pubis*. These three bones cooperate with one another (they typically ossify into a single "hip bone" structure by the age of 25) so as to form the acetabular cup. The acetabular cup receives the head of the femur.

Both the head of the femur and the acetabular cup are covered with a layer of articular cartilage which protects the underlying bone and facilitates motion. See FIG. 6.

Various ligaments and soft tissue serve to hold the ball of the femur in place within the acetabular cup. More particularly, and looking now at FIGS. 7 and 8, the ligamentum teres extends between the ball of the femur and the base of the acetabular cup. As seen in FIG. 9, a labrum is disposed about the perimeter of the acetabular cup. The labrum serves to increase the depth of the acetabular cup and effectively establishes a suction seal between the ball of the femur and the rim of the acetabular cup, thereby helping to hold the head of the femur in the acetabular cup. In addition, and looking now at FIG. 10, a fibrous capsule extends between the neck of the femur and the rim of the acetabular cup, effectively sealing off the ball-and-socket members of the hip joint from the remainder of the body. The foregoing structures are encompassed and reinforced by a set of three main ligaments (i.e., the iliofemoral ligament, the ischiofemoral ligament and the pubofemoral ligament) which extend between the femur and the hip. See FIGS. 11 and 12.

Pathologies of the Hip Joint

As noted above, the hip joint is susceptible to a number of different pathologies. These pathologies can have both congenital and injury-related origins.

By way of example but not limitation, one important type of congenital pathology of the hip joint involves impingement between the neck of the femur and the rim of the acetabular cup. In some cases, and looking now at FIG. 13, this impingement can occur due to irregularities in the geometry of the femur. This type of impingement is sometimes referred to as a cam-type femoroacetabular impingement (i.e., a cam-type FAI). In other cases, and looking now at FIG. 14, the impingement can occur due to irregularities in the geometry of the acetabular cup. This latter type of impingement is sometimes referred to as a pincer-type femoroacetabular impingement (i.e., a pincer-type FAI). Impingement can result in a reduced range of motion, substantial pain and, in some cases, significant deterioration of the hip joint.

By way of further example but not limitation, another important type of congenital pathology of the hip joint involves defects in the articular surface of the ball and/or the articular surface of the acetabular cup. Defects of this type sometimes start out fairly small but often increase in size over time, generally due to the dynamic nature of the hip joint and also due to the weight-bearing nature of the hip joint. Articular defects can result in substantial pain, induce or exacerbate arthritic conditions and, in some cases, cause significant deterioration of the hip joint.

By way of further example but not limitation, one important type of injury-related pathology of the hip joint involves trauma to the labrum. More particularly, in many cases, an accident or a sports-related injury can result in the labrum being torn away from the rim of the acetabular cup, typically with a tear running through the body of the labrum. See FIG. 15. These types of injuries can be very painful for the patient and, if left untreated, can lead to substantial deterioration of the hip joint.

The General Trend Toward Treating Joint Pathologies Using Minimally-Invasive, and Earlier, Interventions The current trend in orthopedic surgery is to treat joint pathologies using minimally-invasive techniques. By way of example but not limitation, it is common to re-attach ligaments in the shoulder joint using minimally-invasive, "keyhole" techniques which do not require laying open the capsule of the shoulder joint. By way of further example but not limitation, it is common to repair torn meniscal cartilage in the knee joint, and/or to replace ruptured ACL ligaments in the knee joint, using minimally-invasive techniques. While such minimally-invasive approaches can require additional training on the part of the surgeon, such procedures generally offer substantial advantages for the patient and have now become the standard of care for many shoulder joint and knee joint pathologies.

In addition to the foregoing, due to the widespread availability of minimally-invasive approaches for treating pathologies of the shoulder joint and knee joint, the current trend is to provide such treatment much earlier in the lifecycle of the pathology, so as to address patient pain as soon as possible and so as to minimize any exacerbation of the pathology itself. This is in marked contrast to traditional surgical practices, which have generally dictated postponing surgical procedures as long as possible so as to spare the patient from the substantial trauma generally associated with invasive surgery.

Treatment for Pathologies of the Hip Joint

Unfortunately, minimally-invasive treatments for pathologies of the hip joint have lagged far behind minimally-invasive treatments for pathologies of the shoulder joint and knee joint. This is generally due to (i) the geometry of the hip joint itself, and (ii) the nature of the pathologies which must typically be addressed in the hip joint.

More particularly, the hip joint is generally considered to be a "tight" joint, in the sense that there is relatively little room to maneuver within the confines of the joint itself. This is in marked contrast to the knee joint, which is generally considered to be relatively spacious when compared to the hip joint. As a result, it is relatively difficult for surgeons to perform minimally-invasive procedures on the hip joint.

Furthermore, the natural pathways for entering the interior of the hip joint (i.e., the pathways which naturally exist between adjacent bones) are generally much more constraining for the hip joint than for the shoulder joint or the knee joint. This limited access further complicates effectively performing minimally-invasive procedures on the hip joint.

In addition to the foregoing, the nature and location of the pathologies of the hip joint also complicate performing minimally-invasive procedures. By way of example but not limitation, consider a typical detachment of the labrum in the hip joint. In this situation, instruments must generally be introduced into the joint space using an angle of approach which is set at approximately a right angle to the angle of re-attachment. This makes drilling into bone, for example, much more complex than where the angle of approach is effectively aligned with the angle of re-attachment, such as is frequently the case in the shoulder joint. Furthermore, the working space within the hip joint is typically extremely limited, further complicating repairs where the angle of approach is not aligned with the angle of re-attachment.

As a result of the foregoing, minimally-invasive hip joint procedures are still relatively difficult, and patients must frequently manage their hip joint pathologies for as long as possible, until a partial or total hip replacement can no longer be avoided, whereupon the procedure is generally done as a highly-invasive, open procedure, with all of the disadvantages associated with highly-invasive, open procedures.

As a result, there is a pressing need for improved methods and apparatus for reconstructing the hip joint.

Issues Relating to the Treatment of Cam-Type Femoroacetabular Impingement

As noted above, hip arthroscopy is becoming increasingly more common in the diagnosis and treatment of various hip pathologies. However, due to the anatomy of the hip joint and the pathologies associated with the same, hip arthroscopy is currently practical for only selected pathologies and, even then, hip arthroscopy has generally met with limited success.

One procedure which is sometimes attempted arthroscopically relates to femoral debridement for treatment of cam-type femoroacetabular impingement (i.e., cam-type FAI). More particularly, with cam-type femoroacetabular impingement, irregularities in the geometry of the femur can lead to impingement between the femur and the rim of the acetabular cup. Treatment for cam-type femoroacetabular impingement typically involves debriding the femoral neck and/or head, using tools such as burrs, to remove the bony deformities causing the impingement. In this respect it should be appreciated that it is important to debride the femur carefully, since only bone which does not conform to the desired geometry should be removed, in order to ensure positive results as well as to minimize the possibility of bone fracture after treatment.

For this reason, when debridement is performed as an open surgical procedure, surgeons generally use pre-shaped curvature templates to guide them in removing the appropriate amount of bone from the femur.

However, when the debridement procedure is attempted arthroscopically, conventional curvature templates cannot be passed through the narrow keyhole incision, and hence debridement templates are not available to the surgeon for reshaping the bone surface. As a result, the debridement must be effected freehand. In this setting, it is generally quite difficult for the surgeon to determine exactly how much bone should be removed, and whether the shape of the remaining bone has the desired geometry.

Accordingly, a primary object of the present invention is to provide the surgeon with arthroscopic debridement templates which can be used during an arthroscopic debridement procedure to treat cam-type femoroacetabular impingement.

SUMMARY OF THE INVENTION

The present invention comprises the provision and use of a novel arthroscopic debridement template which can be used during an arthroscopic debridement procedure to treat cam-type femoroacetabular impingement.

In one preferred form of the invention, there is provided apparatus for use in debriding a bone, said apparatus comprising:

an arthroscopic debridement template comprising a body reconfigurable between (i) a first configuration having a first profile and comprising an arc matching the desired curvature of the bone after debridement, and (ii) a second configuration having a second profile, wherein said second profile is smaller than said first profile.

In another preferred form of the invention, there is provided apparatus for use in debriding a bone, said apparatus comprising:

an arthroscopic debridement template comprising a plurality of fingers reconfigurable between (i) a first configuration having a first profile and defining an arc matching the desired curvature of the bone after debridement, and (ii) a second configuration having a second profile, wherein said second profile is smaller than said first profile.

In another preferred form of the invention, there is provided apparatus for use in debriding a bone, said apparatus comprising:

an elongated body comprising at least one light-emitting element for projecting an optical arthroscopic debridement template onto the bone, wherein said optical arthroscopic debridement template comprises a first pattern when projected onto an area of the bone having a regular surface and a second pattern when projected onto an area of the bone having an irregular surface.

In another preferred form of the invention, there is provided apparatus for use in debriding a bone, said apparatus comprising:

an arthroscopic debridement template comprising at least one marker for disposition within the bone, wherein said at least one marker comprises a body discernable from bone.

In another preferred form of the invention, there is provided a method for debriding a bone, said method comprising:

providing apparatus comprising:

an arthroscopic debridement template comprising a body reconfigurable between (i) a first configuration having a first profile and comprising an arc matching the desired curvature of the bone after debridement, and (ii) a second configuration having a second profile, wherein said second profile is smaller than said first profile;

configuring said arthroscopic debridement template in said second configuration;

advancing said arthroscopic debridement template to a debridement site;

reconfiguring said arthroscopic debridement template from said second configuration to said first configuration; and debriding the bone using said arthroscopic debridement template for guidance.

In another preferred form of the invention, there is provided a method for debriding a bone, said method comprising:

providing apparatus comprising:

an arthroscopic debridement template comprising a plurality of fingers reconfigurable between (i) a first configuration having a first profile and defining an arc matching the desired curvature of the bone after debridement, and (ii) a second configuration having a second profile, wherein said second profile is smaller than said first profile;

configuring said arthroscopic debridement template in said second configuration;

advancing said arthroscopic debridement template to a debridement site;

reconfiguring said arthroscopic debridement template from said second configuration to said first configuration; and debriding the bone using said arthroscopic debridement template for guidance.

In another preferred form of the invention, there is provided a method for debriding a bone, said method comprising:

providing apparatus comprising:

an elongated body comprising at least one light-emitting element for projecting an optical arthroscopic debridement template onto the bone, wherein said optical arthroscopic debridement template comprises a first pattern when projected onto an area of the bone having a regular surface and a second pattern when projected onto an area of the bone having an irregular surface;

projecting said optical arthroscopic debridement template onto the bone;

debriding the bone using said arthroscopic debridement template for guidance.

In another preferred form of the invention, there is provided a method for debriding a bone, said method comprising:

providing apparatus comprising:

an arthroscopic debridement template comprising at least one marker for disposition within the bone, wherein said at least one marker comprises a body discernable from bone;

positioning said at least one marker within the bone that is to be debrided, said at least one marker being set so as to demarcate at least one of (i) the area of bone to be debrided, and (ii) the depth of bone to be debrided; and debriding the bone using said arthroscopic debridement template for guidance.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1A:
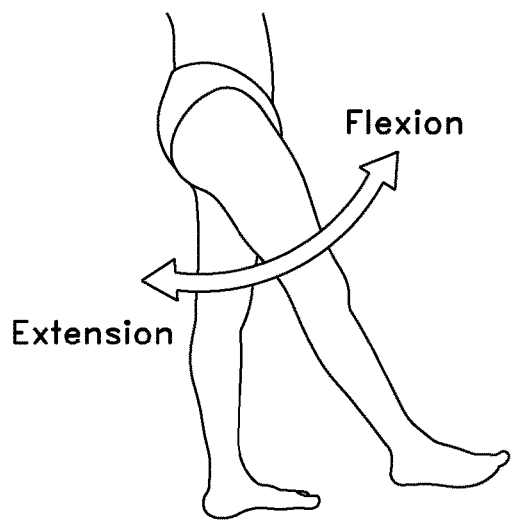
FIGS. 1A-1D are schematic views showing various aspects of hip motion.
Figure 1B:
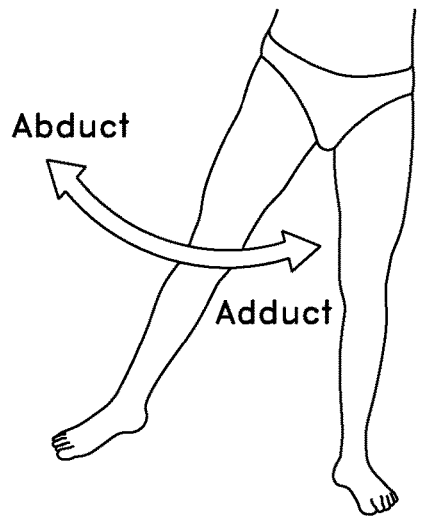
Figure 1C:
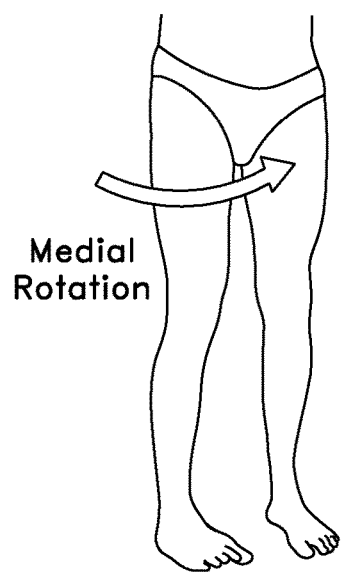
Figure 1D:
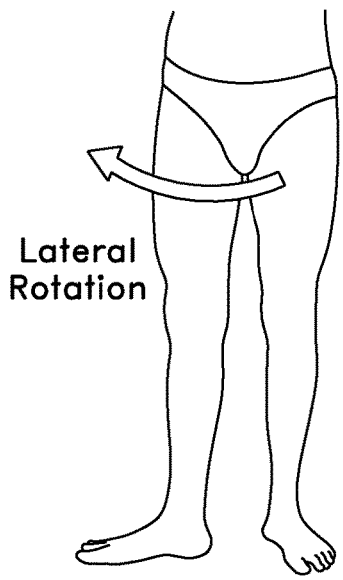
Figure 2:
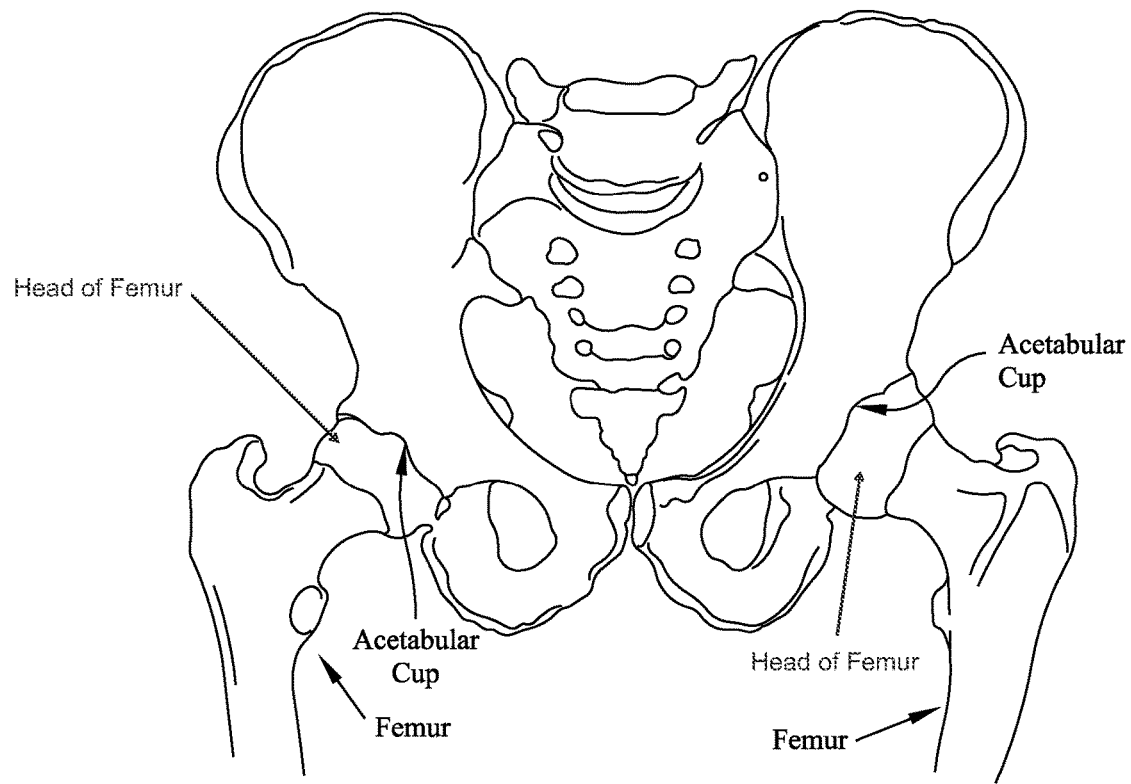
FIG. 2 is a schematic view showing bone structures in the region of the hip joint.
Figure 3:
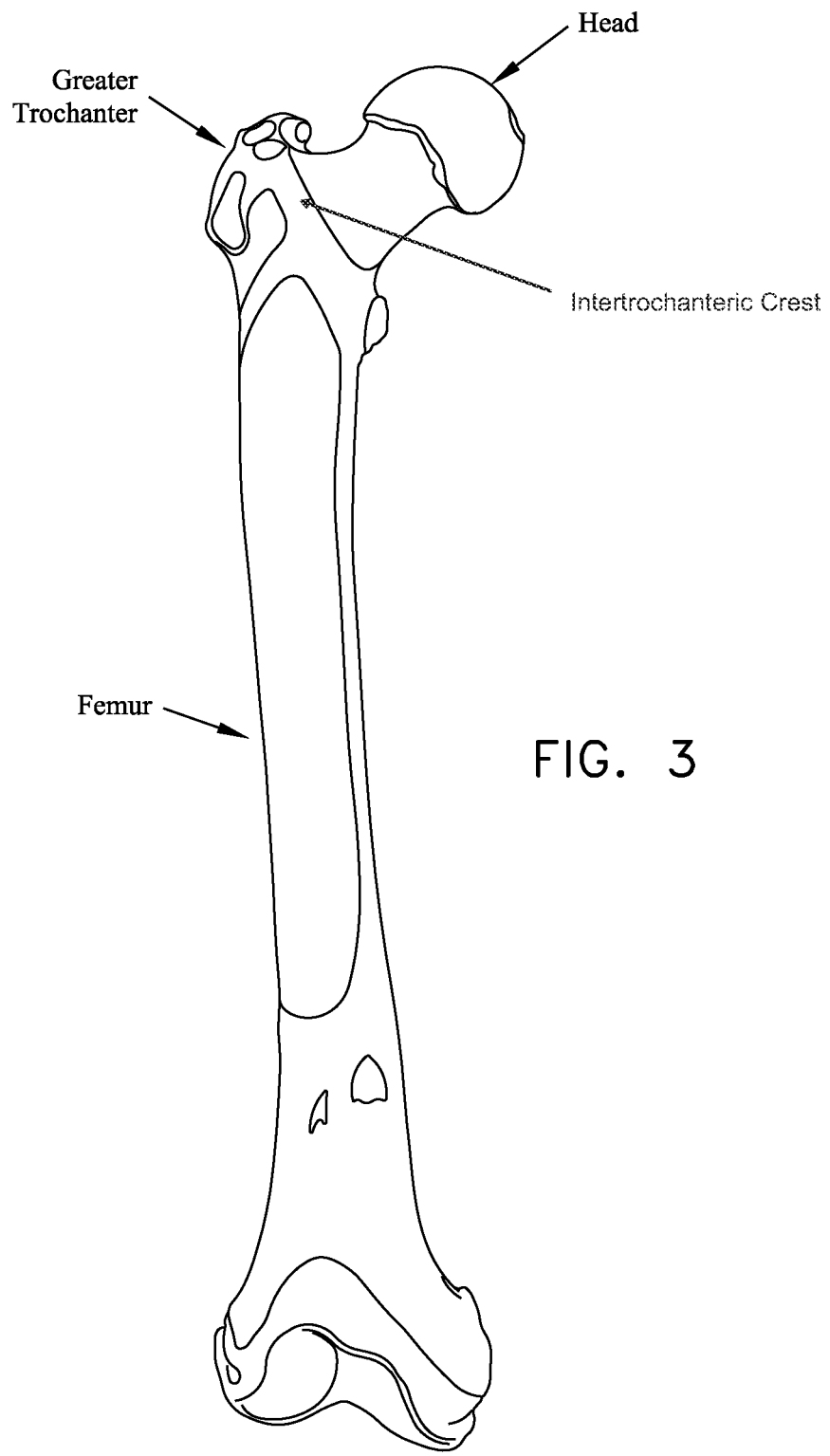
FIG. 3 is a schematic anterior view of the femur.
Figure 4:
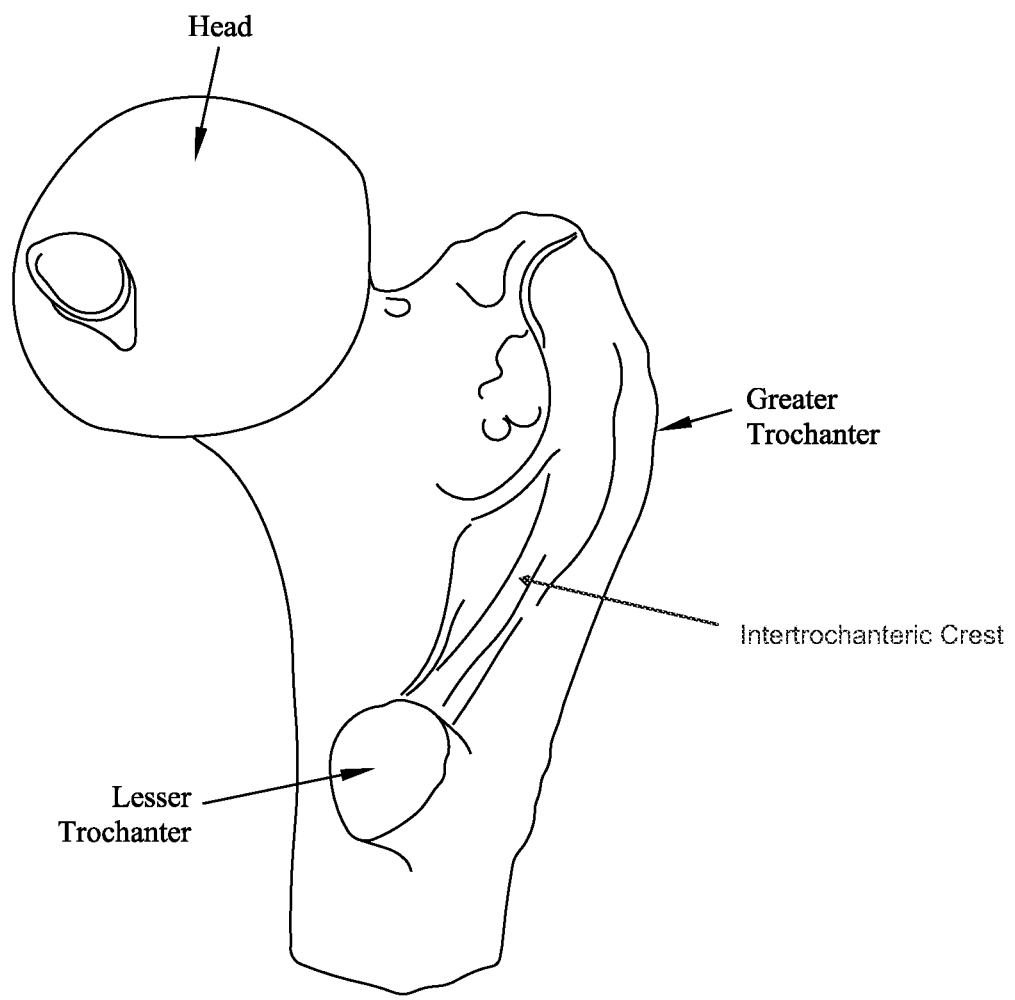
FIG. 4 is a schematic posterior view of the top end of the femur.
Figure 5:
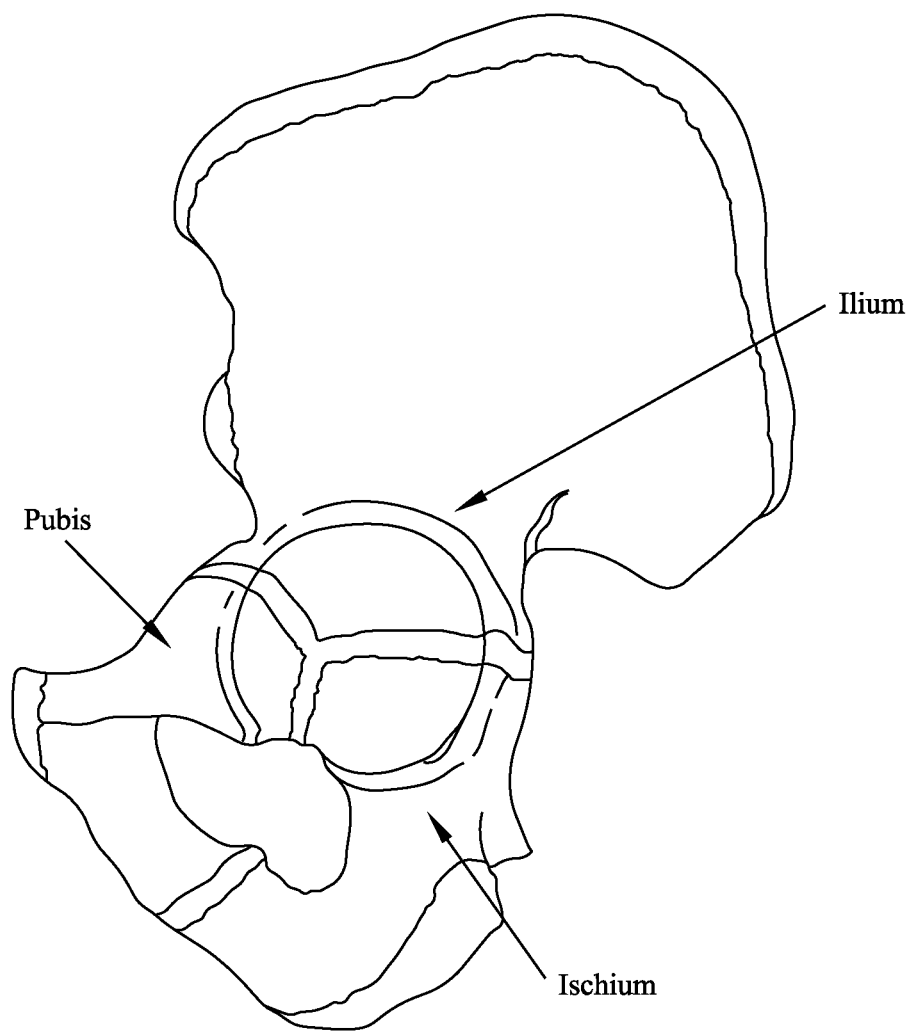
FIG. 5 is a schematic view of the pelvis.
Figure 6:
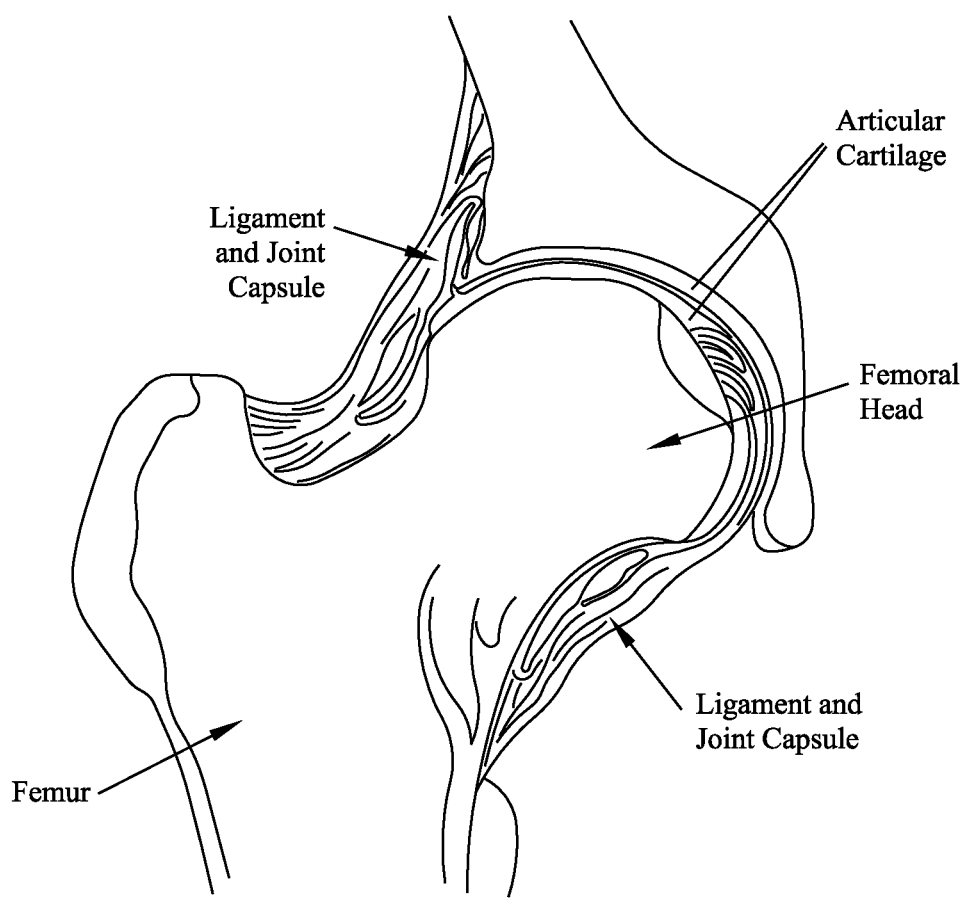
FIGS. 6-12 are schematic views showing bone and soft tissue structures in the region of the hip joint.
Figure 7:
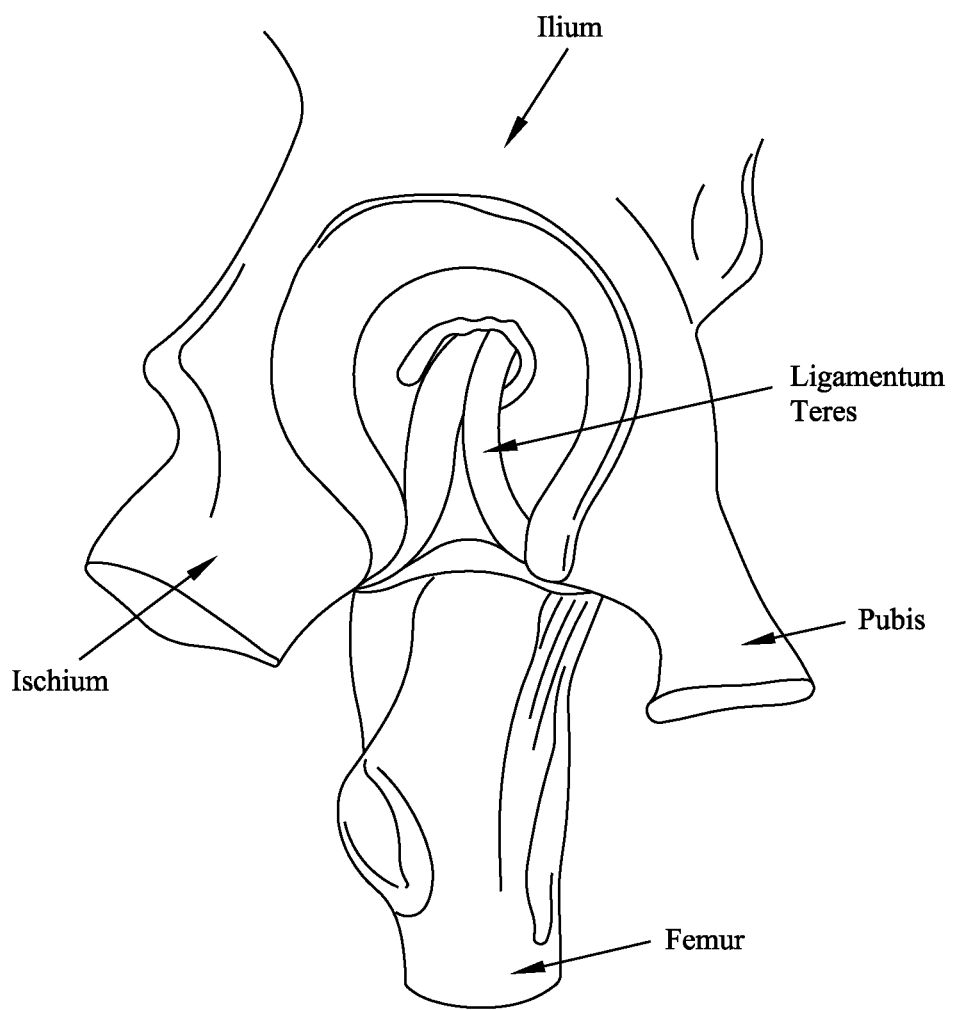
Figure 8:
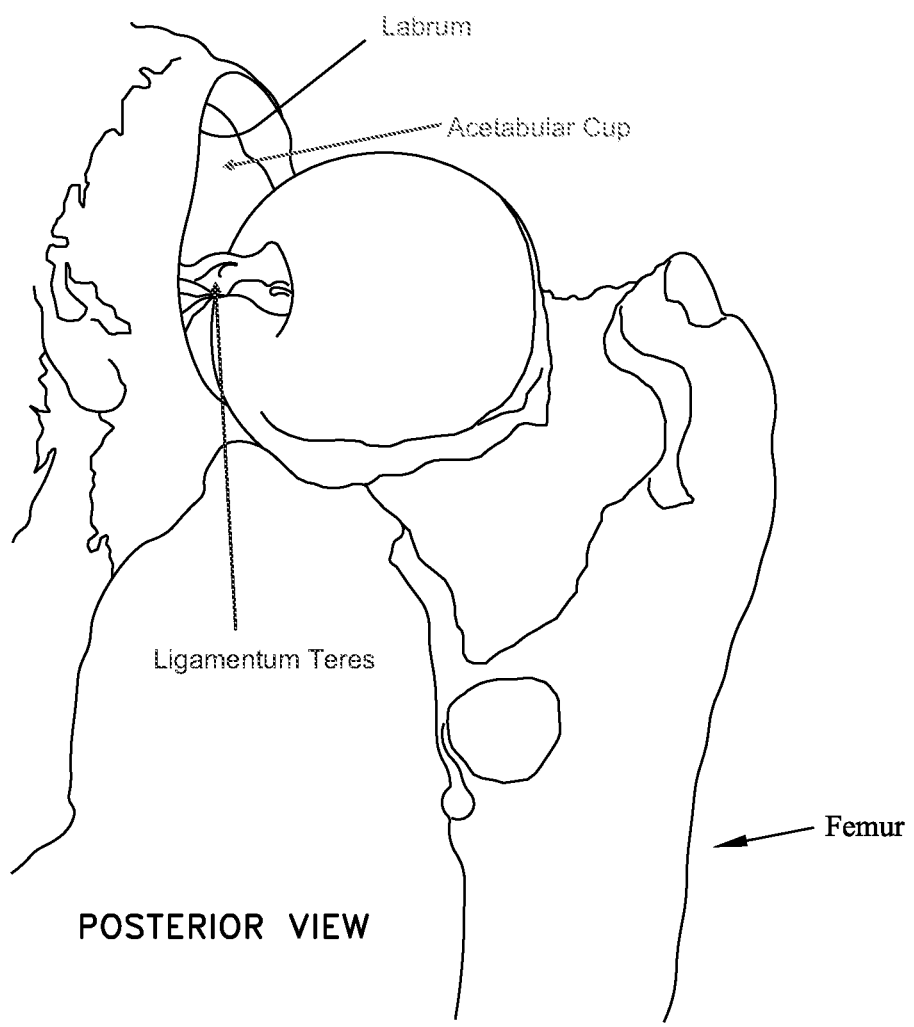
Figure 9:
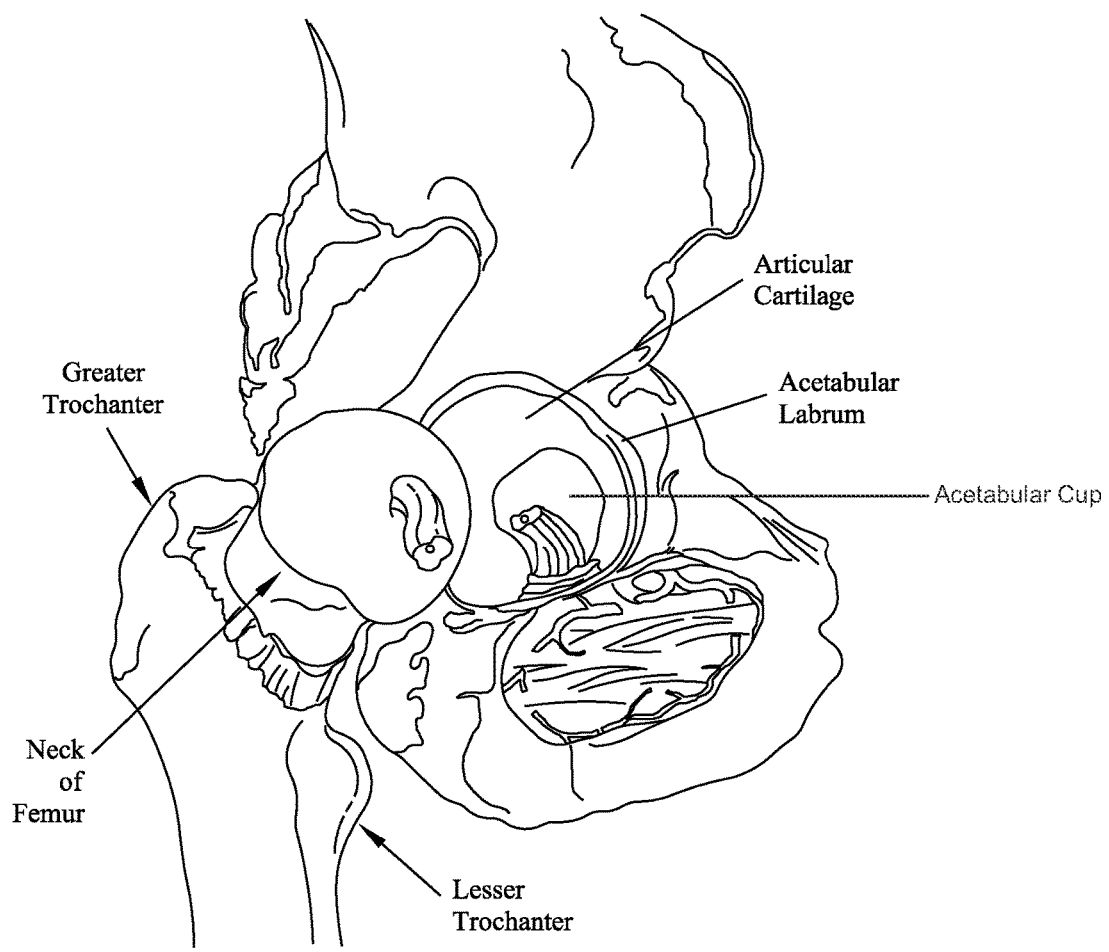
Figure 10:
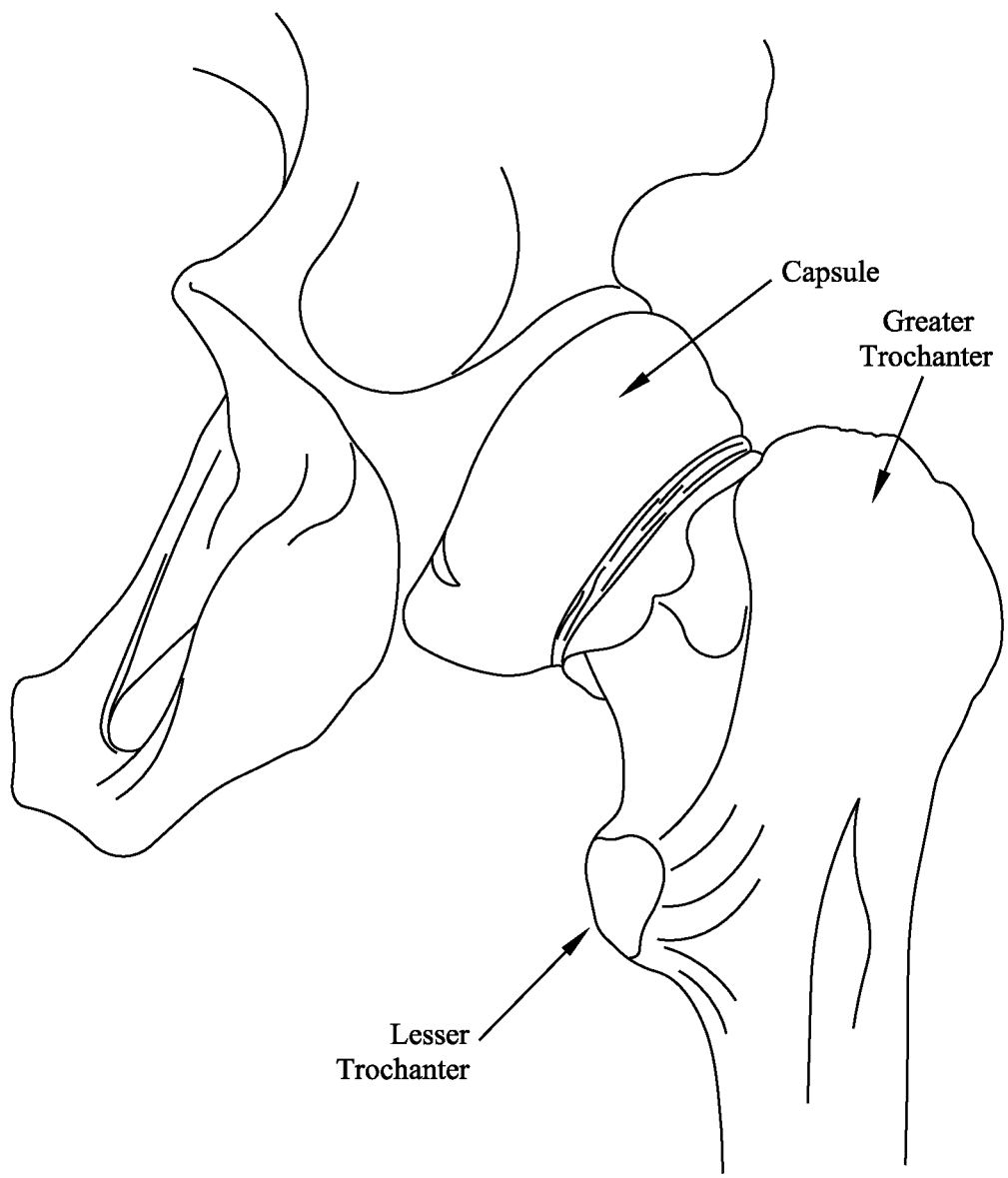
Figure 11:
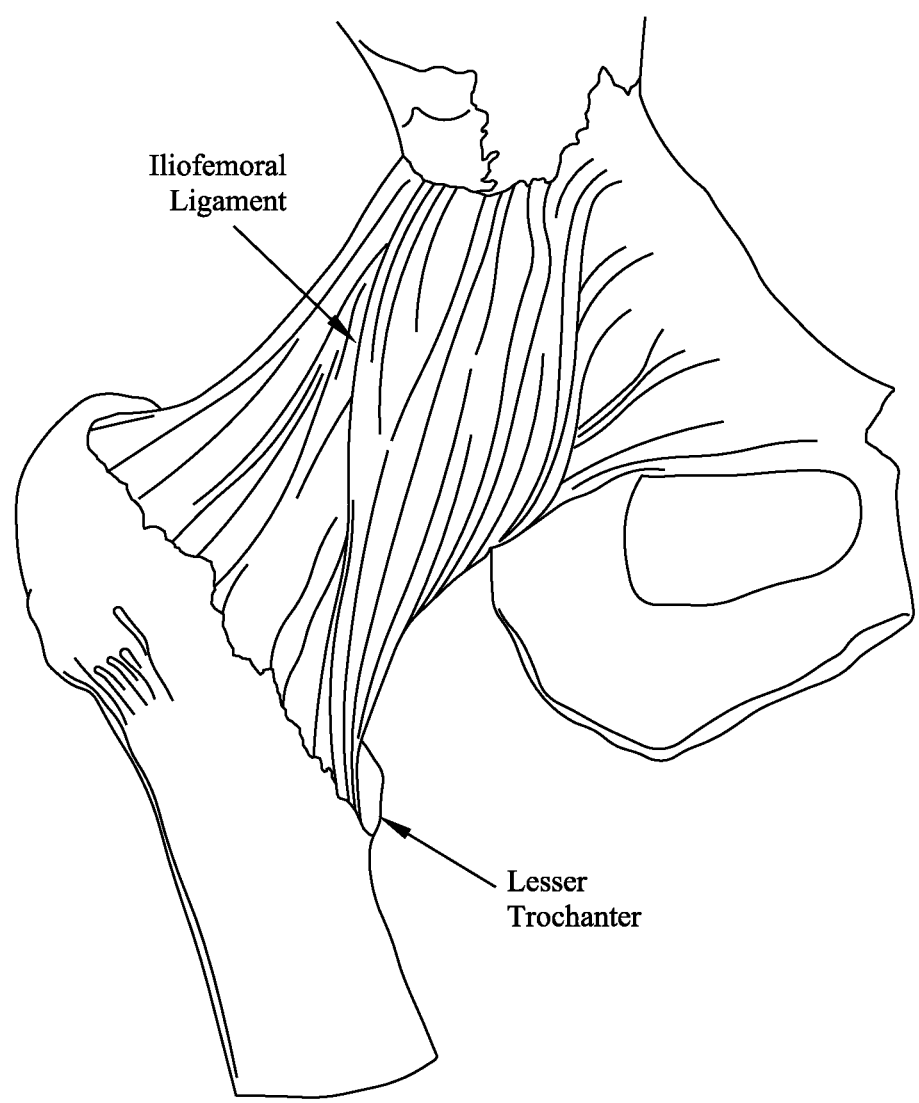
Figure 12:
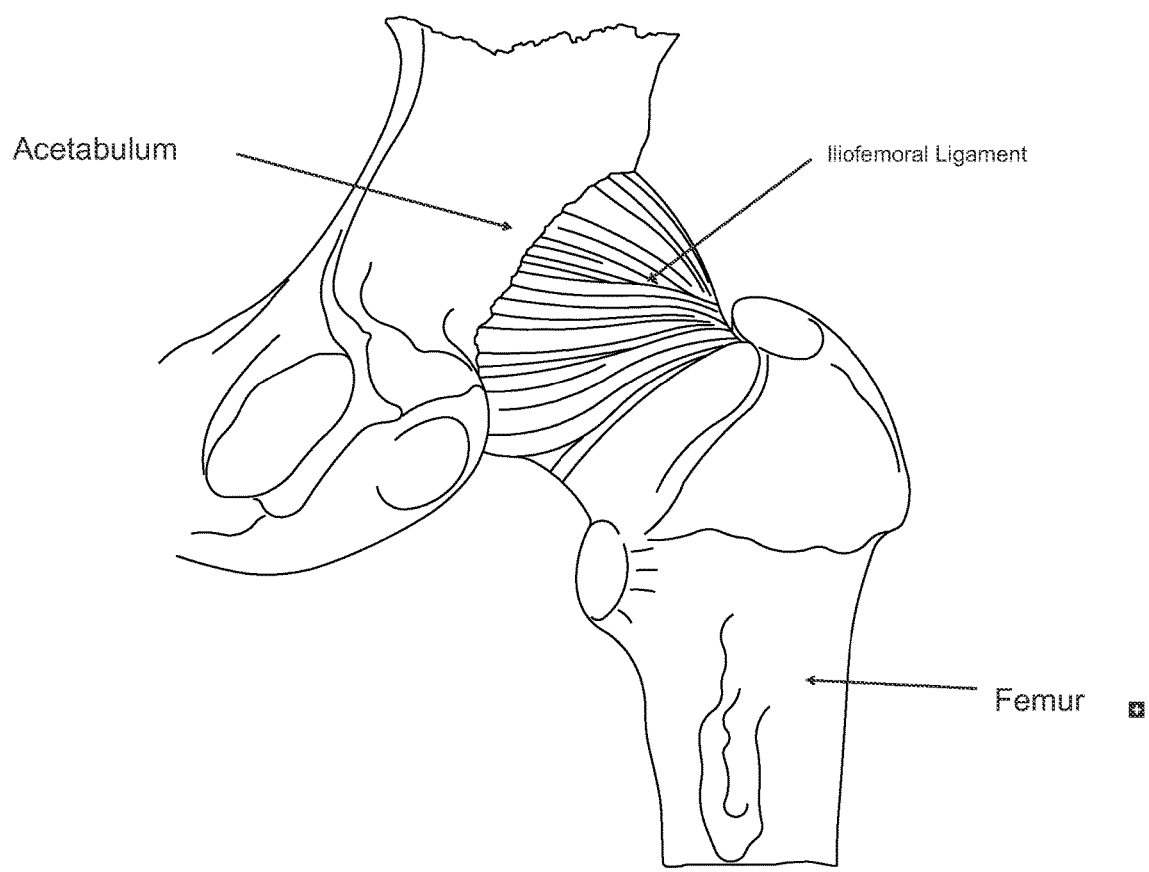
Figure 13:
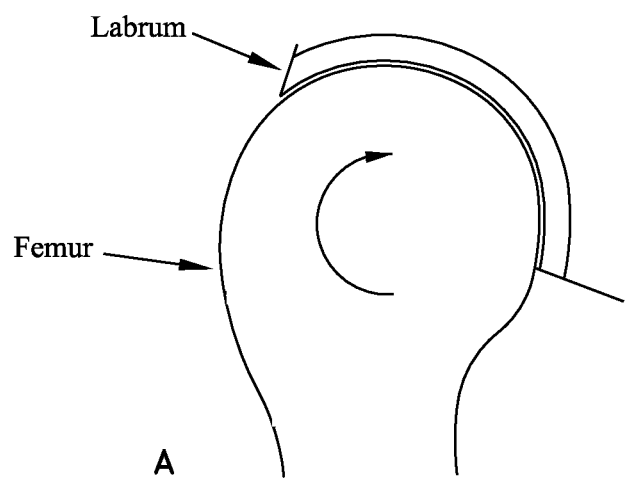
FIG. 13 is a schematic view showing cam-type femoroacetabular impingement (i.e., cam-type FAI)
Figure 13:
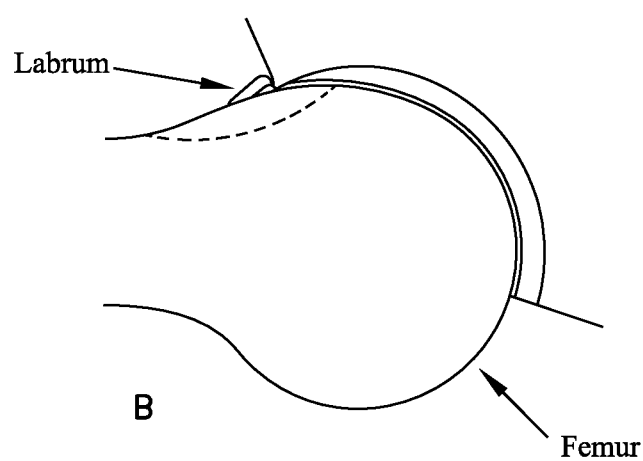
Figure 14:
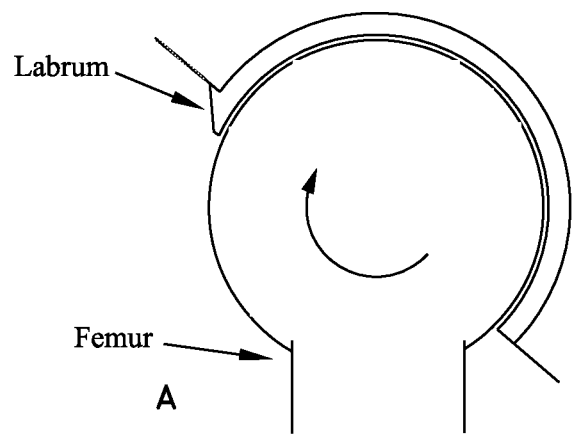
FIG. 14 is a schematic view showing pincer-type femoroacetabular impingement (i.e., pincer-type FAI)
Figure 14:
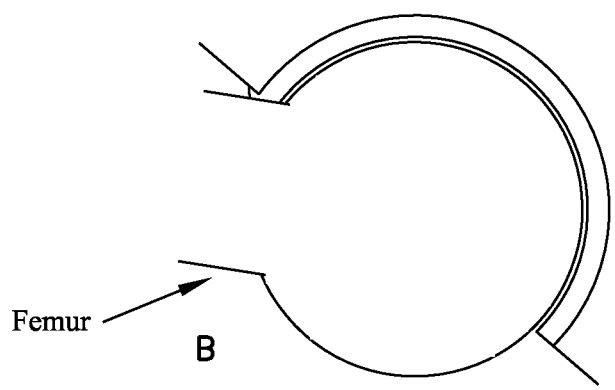
Figure 15:
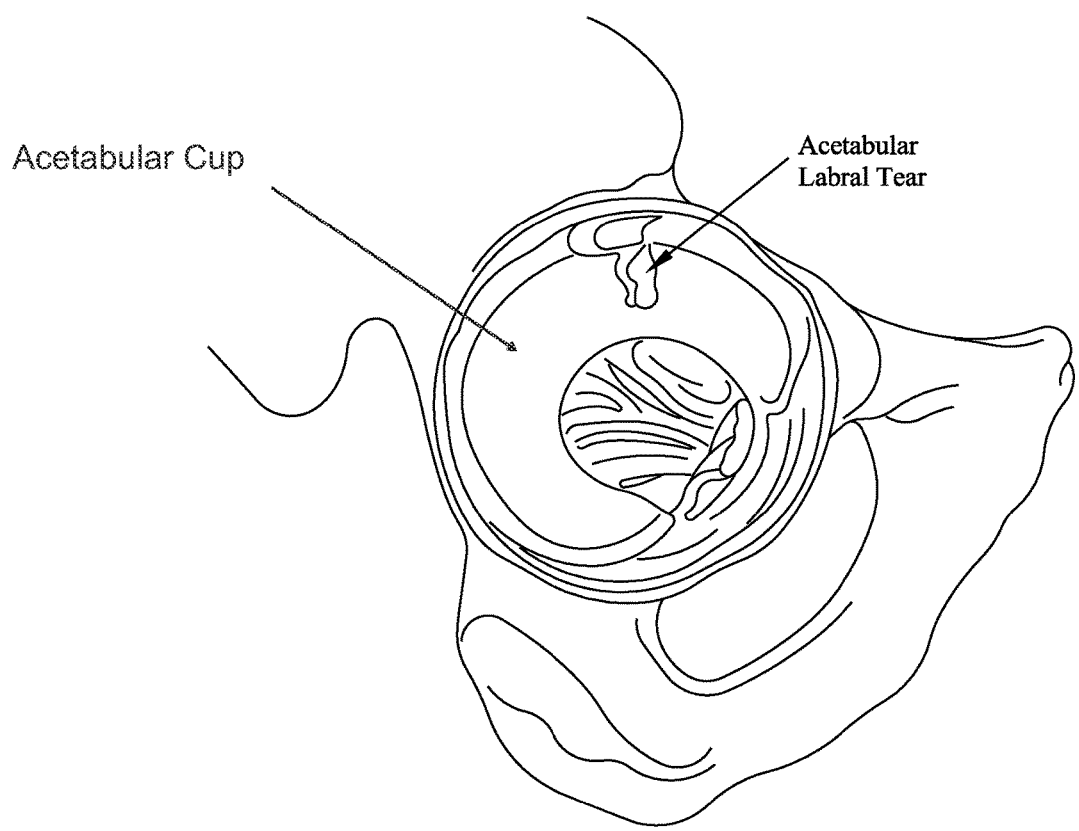
FIG. 15 is a schematic view showing a labral tear.

The present invention comprises the provision and use of a novel arthroscopic debridement template which can be used during an arthroscopic debridement procedure to treat cam-type femeroacetabular impingement.

As will hereinafter be discussed, the present invention provides mechanical arthroscopic debridement templates, optical arthroscopic debridement templates and arthroscopic debridement templates incorporating a bone cutting tool.

Mechanical Arthroscopic Debridement Templates

In one preferred form of the invention, there is provided a mechanical arthroscopic debridement template. In this form of the invention, the arthroscopic debridement template is mounted on the distal end of an insertable tool and the arthroscopic debridement template is capable of being reconfigurable between (i) a reduced configuration so that the arthroscopic debridement template may be moved to, and withdrawn from, an arthroscopic surgical site, and (ii) an expanded configuration so that the arthroscopic debridement template may provide guidance to the surgeon during the bone reshaping process.

In one preferred form of the invention, the arthroscopic debridement template is mounted on the distal end of an insertable tool so that (i) the arthroscopic debridement template can be retracted into the insertable tool when the arthroscopic debridement template is to be moved to, and removed from, the surgical site, and (ii) the arthroscopic debridement template can be projected out of the distal end of the insertable tool when the arthroscopic debridement template is to be used at the surgical site (e.g., at the femoral neck, at the femoral head, at the transition between the femoral neck and the femoral head, etc.) so as to guide a surgeon in reshaping the bone surface.

The foregoing approach facilitates introducing the arthroscopic debridement template to the surgical site through a narrow keyhole incision, yet permits the arthroscopic debridement template to be expanded to its full working shape at the surgical site for use during the debridement procedure. Among other things, the apparatus is preferably configured so that the apparatus can be introduced through a standard arthroscopic access cannula (e.g., 4 mm to 8.5 mm in diameter), and the apparatus is preferably configured so that the apparatus can be articulated and manipulated as necessary so that the arthroscopic debridement template can be appropriately positioned adjacent to the bone which is to be debrided.

In one preferred form of the invention, the surgeon is provided with a kit comprising various arthroscopic debridement templates, with the various arthroscopic debridement templates being sized to address a variety of different patient anatomies. In one form of the invention, the various arthroscopic debridement templates are each provided with their own associated insertable tool. In another form of the invention, the various arthroscopic debridement templates can be selectively mated to a common insertable tool.

The arthroscopic debridement template of the present invention can be formed with a variety of constructions without departing from the scope of the present invention. A number of these exemplary constructions will now be discussed in greater detail.

Figure 16:
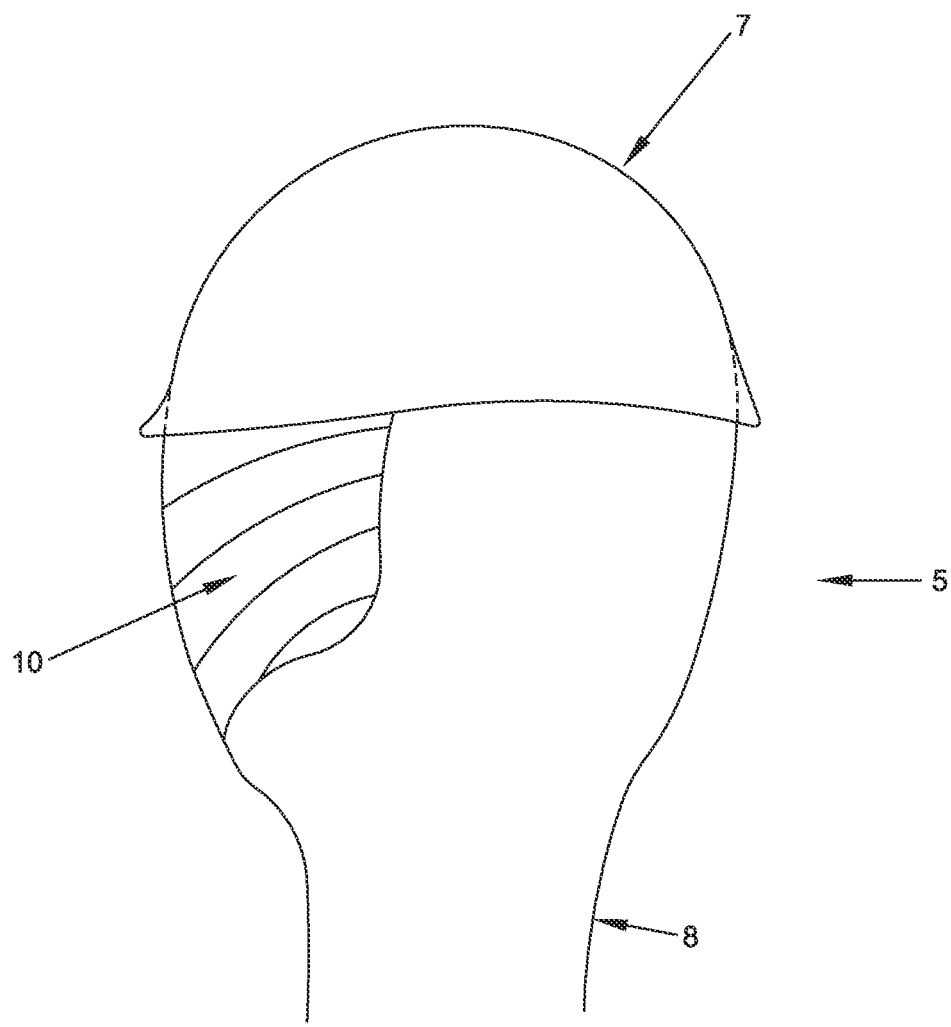
FIG. 16 is a schematic view showing the head and neck of a femur and a cam-type femeroacetabular impingement site.

More particularly, FIG. 16 shows a schematic view of a femur 5 comprising a femoral head 7 and a femoral neck 8, and illustrates a cam-type femeroacetabular impingement site 10 which needs to be debrided in order to treat the cam-type femeroacetabular impingement.

Figure 17:
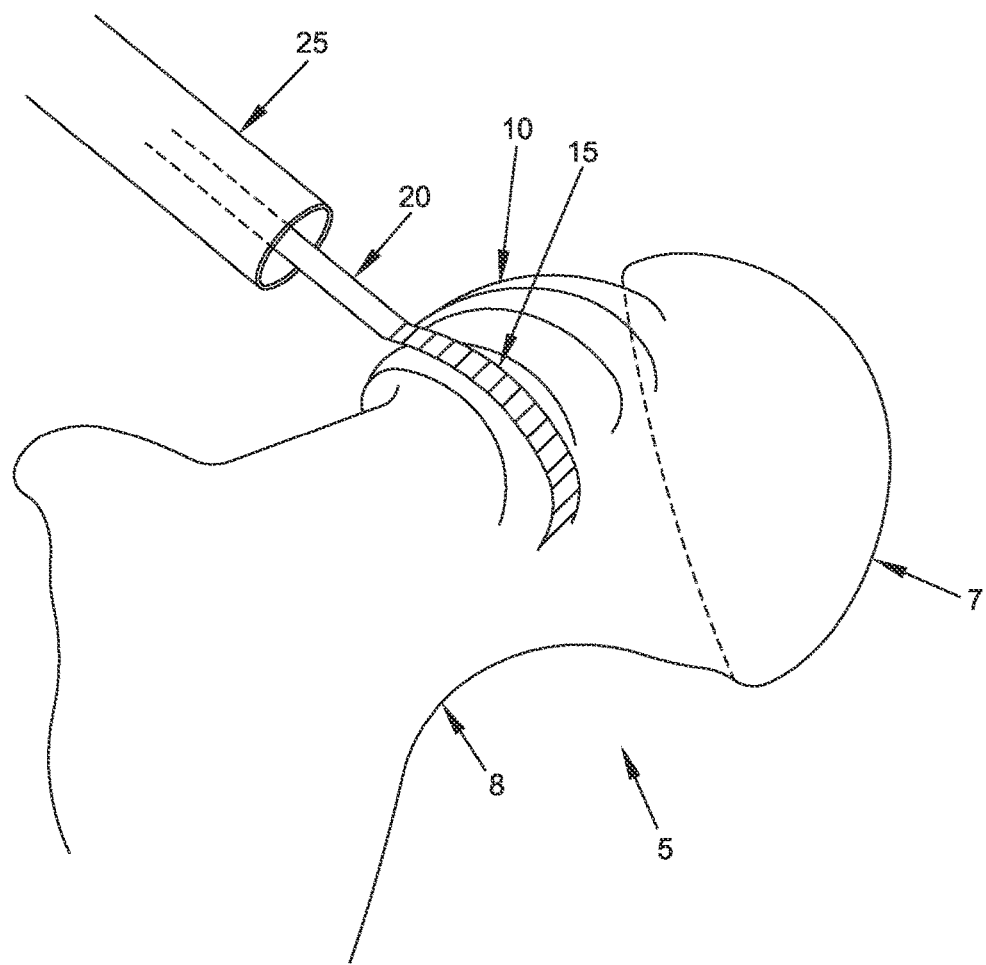
FIG. 17 is a schematic view of an arthroscopic debridement template formed in accordance with the present invention.

FIG. 17 shows a one-piece arthroscopic debridement template 15. Arthroscopic debridement template 15 is mounted at the distal end of a shaft 20 and is advanced through an arthroscopic access cannula 25 to the impingement site 10 (e.g., at the femoral neck, at the femoral head, at the transition between the femoral neck and the femoral head, etc.). The one-piece arthroscopic debridement template 15 is formed with a pre-determined curved geometry which matches the desired bone geometry. Thus, during debridement, arthroscopic debridement template 15 can be placed directly against the bone. This allows the surgeon to compare the patient's current bone geometry with the desired bone geometry (which is reflected by the configuration of arthroscopic debridement template 15) and, in the process, to be guided with respect to the amount of bone which is to be removed. In order to permit arthroscopic debridement template 15 to be passed through the narrow arthroscopic access cannula 25, arthroscopic debridement template 15 is preferably formed out of an elastic material (e.g., a superelastic material such as Nitinol). This permits arthroscopic debridement template 15 to assume one configuration (e.g., long and narrow) while passing through arthroscopic access cannula 25, and then assume another configuration (e.g., broad and curved) when at the surgical site.

Figures 17A, 17B, 17C:
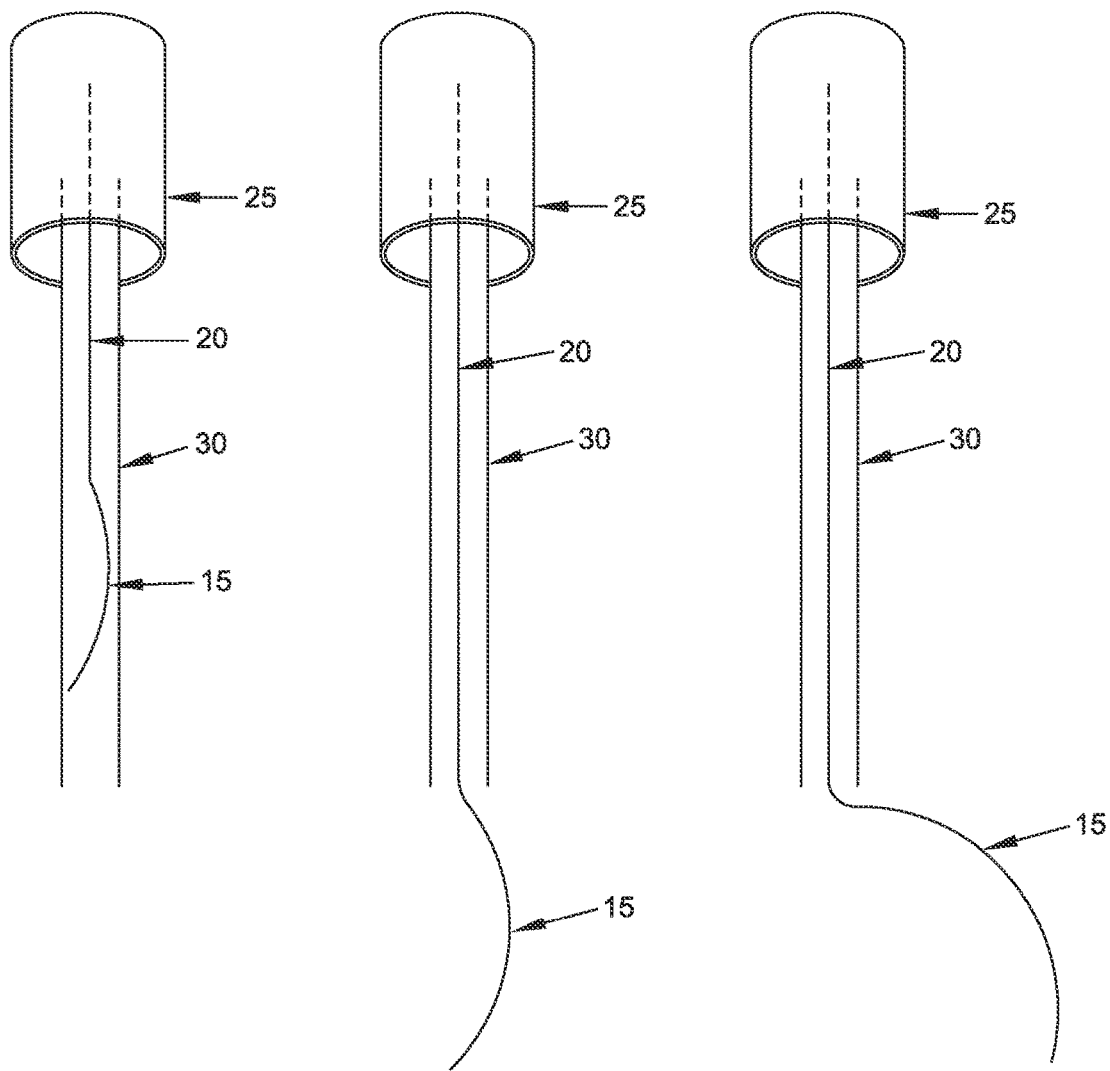
FIGS. 17A-17C are schematic views of another arthroscopic debridement template formed in accordance with the present invention.

In another form of the present invention, and looking now at FIGS. 17A-17C, the novel apparatus comprises a multi-component construction whereby arthroscopic debridement template 15 is secured to a shaft 20 and telescopically housed in an inserter tube 30 which fits through arthroscopic access cannula 25. Arthroscopic debridement template 15 is retracted within inserter tube 30 during delivery into the joint space (FIG. 17A) in order to facilitate passage through arthroscopic access cannula 25 and patient anatomy, then extended from inserter tube 30 (FIG. 17B) for use in a bone debridement procedure at the arthroscopic site.

In one form of the invention, arthroscopic debridement template 15 may be aligned with the longitudinal axis of inserter tube 30 (see FIGS. 17A and 17B). Alternatively, in another form of the invention, arthroscopic debridement template 15 may be disposed out of alignment with the longitudinal axis of inserter tube 30 (see FIG. 17C). In such a construction, and looking now at FIG. 17C, arthroscopic debridement template 15 may be biased so as to extend laterally away from the longitudinal axis of inserter tube 30 as arthroscopic debridement template 15 is extended out of inserter tube 30. This construction can be particularly useful where the angle of approach to the surgical site (which is generally dictated by the disposition of arthroscopic cannula 25 within the anatomy) is different from the angle at which arthroscopic debridement template 15 must address the bone.

Figure 18A:
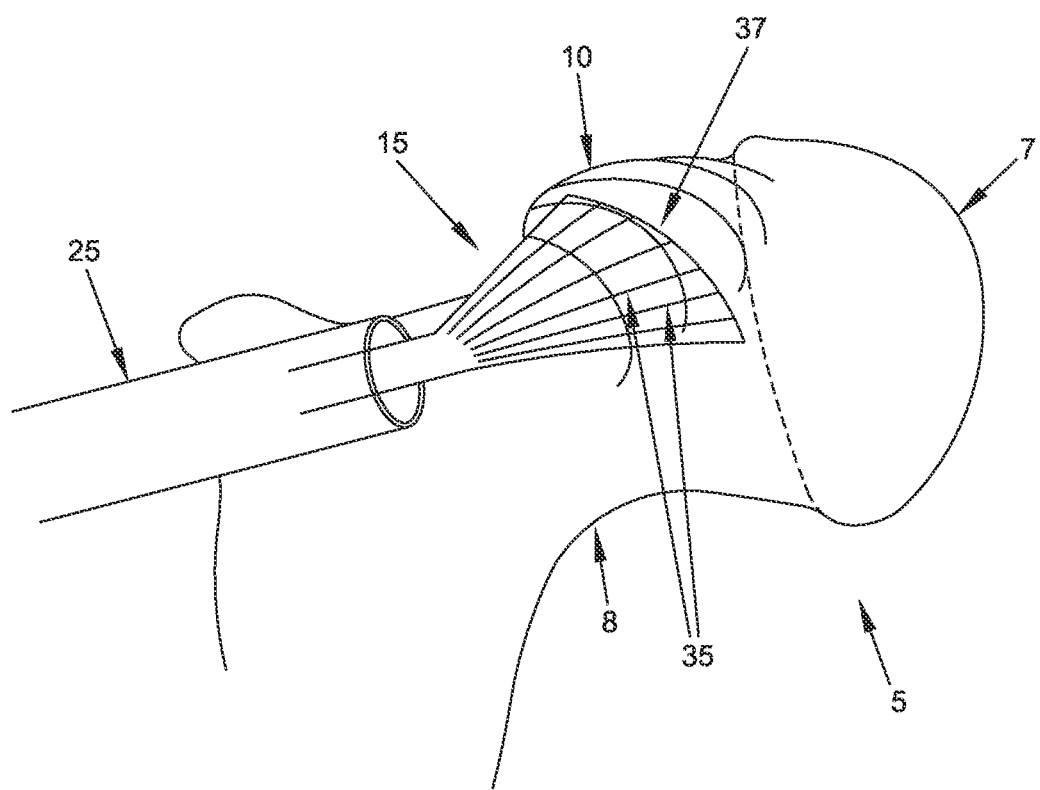
FIGS. 18A and 18B are schematic views of another arthroscopic debridement template formed in accordance with the present invention.
Figure 18B:
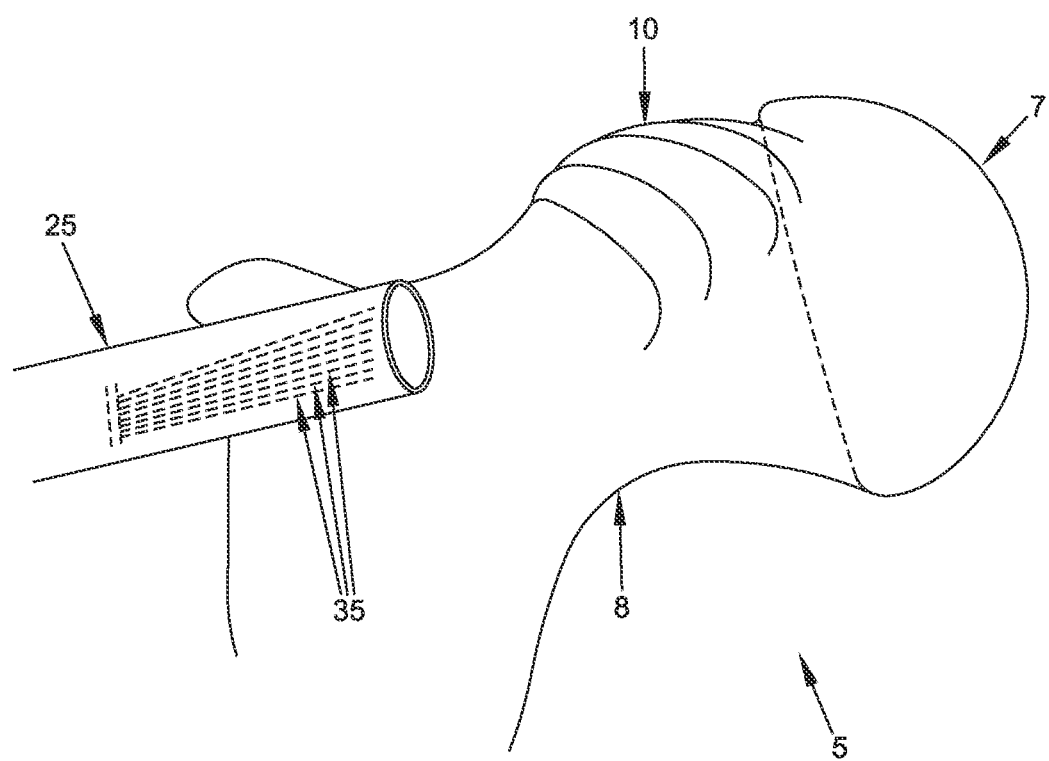

FIGS. 18A and 18B show another configuration for the arthroscopic debridement template 15 of the present invention. More particularly, in this form of the invention, arthroscopic debridement template 15 is formed out of a plurality of fingers (and/or arms) 35 which, in their open configuration (FIG. 18A), collectively form a fan-like structure which is reflective of the desired bone geometry, but which, when in their closed configuration (FIG. 18B), form a narrow bundle-like structure which can be passed through arthroscopic access cannula 25. To this end, fingers 35 are preferably formed out of an elastic material (e.g., a superelastic material such as Nitinol). If desired, the distal ends of two or more of the fingers 35 may be connected together by a filament 37 (FIG. 18A) so as to provide further definition to the fan-like structure collectively defined by fingers 35.

Figure 19A:
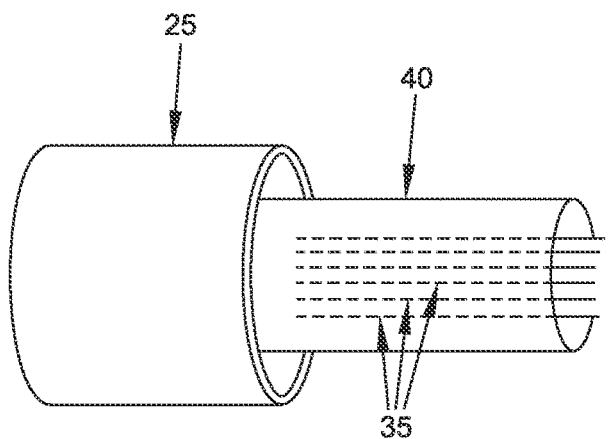
FIGS. 19A and 19B are schematic views of another arthroscopic debridement template formed in accordance with the present invention.
Figure 19B:
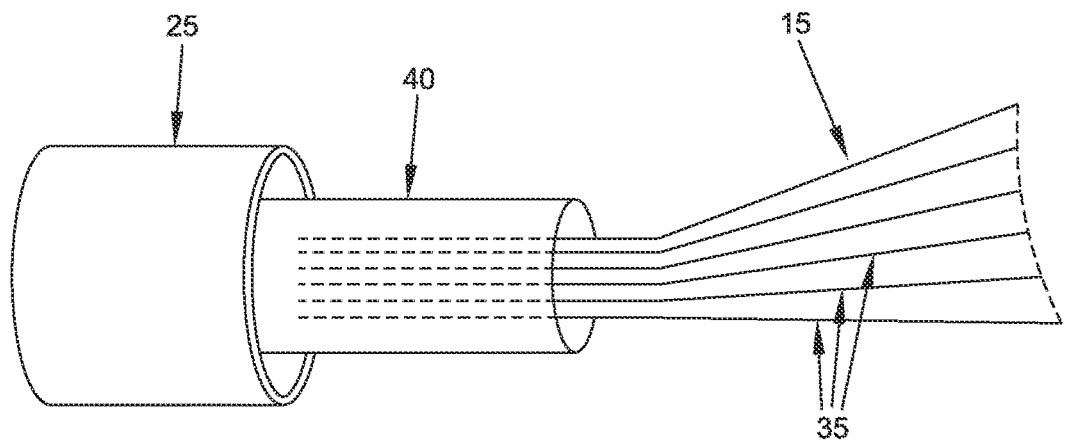

In one preferred form of the invention, the plurality of fingers 35 are telescopically housed in an inserter tube 40 during delivery to the joint space (see FIG. 19A). Once inside the joint space, the plurality of fingers 35 are extended out of inserter tube 40 so as to form the fan-like structure (FIG. 19B) which is to be placed against the bone surface to serve as an arthroscopic debridement template (see FIG. 18A). In this form of the invention, the plurality of fingers 35 are extended out of inserter tube 40 so as to create a single collective structure which can be placed on the bone surface which is to be debrided, whereby to act as a template for the bone debridement procedure.

In one form of the present invention, each of the fingers 35 extends out of inserter tube 40 so as to form a structure of constant radius. In another form of the present invention, each of the fingers 35 extends out of inserter tube 40 so as to form a collective structure of varying radius and/or a compound curve. In yet another form of the present invention, each of the fingers 35 may be variably extended out of inserter tube 40 to various longitudinal positions, whereby to form a collective structure having a variety of radii and/or shapes according to the extent to which each finger 35 is extended out of inserter tube 40. By way of example but not limitation, each of the fingers 35 may have 2 or more longitudinal positions relative to inserter tube 40, wherein each longitudinal position has a different radius of curvature.

Figure 20:
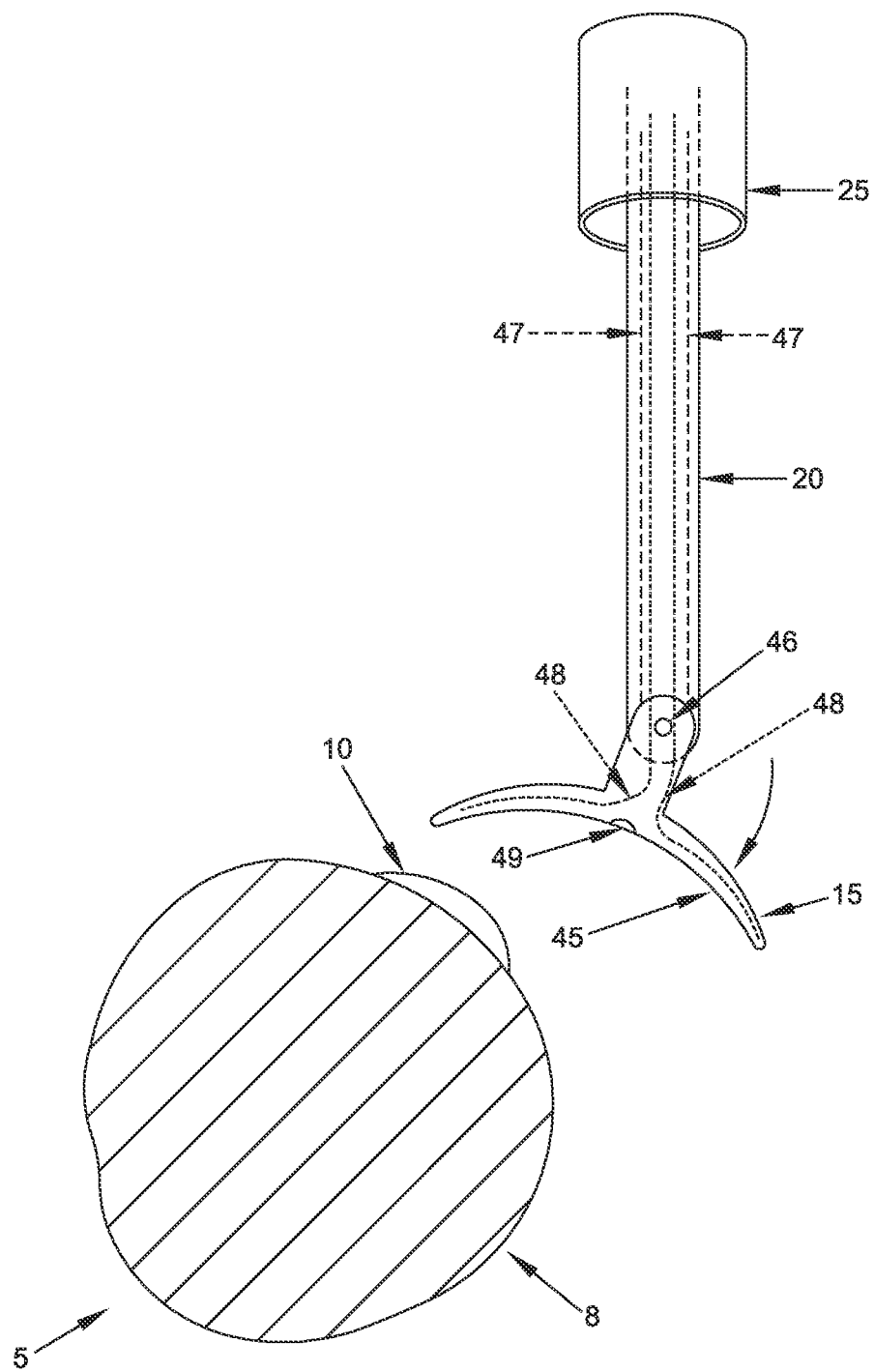
FIG. 20 is a schematic view of an arthroscopic debridement template formed in accordance with the present invention.

In another form of the present invention, and looking now at FIG. 20, arthroscopic debridement template 15 comprises an arc 45 of fixed curvature, wherein arthroscopic debridement template 15 is pivotally mounted to the distal end of a shaft 20. In this form of the invention, arc 45 of arthroscopic debridement template 15 is formed with a pre-determined curved geometry which matches the desired bone geometry. Thus, during the debridement procedure (e.g., at the femoral neck, at the femoral head, at the transition between the femoral neck and the femoral head, etc.), arthroscopic debridement template 15 can be placed against the bone which is to be debrided so that arc 45 of the arthroscopic debridement template 15 sits adjacent to the bone. This allows the surgeon to compare the patient's current bone geometry with the desired bone geometry (which is reflected by arc 45 of arthroscopic debridement template 15), whereby to guide the surgeon in determining the appropriate amount of bone to be debrided.

During the debridement procedure, shaft 20 is used to advance arthroscopic debridement template 15 through an arthroscopic access cannula 25 to the impingement site, so that arc 45 of arthroscopic debridement template 15 approaches the bone (e.g., the femoral neck 8 as shown in FIG. 20). Arc 45 of arthroscopic debridement template 15 may then be pressed up against the bone, such that the surgeon can compare the geometry of the native bone to the geometry desired for the bone (i.e., the curvature of arc 45).

In order to facilitate passage of arthroscopic debridement template 15 through the arthroscopic access cannula 25 and to assist advancing arthroscopic debridement template 15 to the surgical site, arthroscopic debridement template 15 is preferably pivotally connected to the distal end of shaft 20 (e.g., by a pivot pin 46), and the apparatus may further comprise control means 47 (e.g., control wires, push rods, etc. of the sort well known in the art) connecting arthroscopic debridement template 15 to the proximal end of shaft 20 (not shown), so that the surgeon can adjust the disposition of arthroscopic debridement template 15 (and hence adjust the disposition of its arc 45) relative to shaft 20 during the debridement procedure.

It should also be appreciated that, if desired, arthroscopic debridement template 15 can be formed out of a flexible material, and additional control means 48 (e.g., control wires, push rods, etc. of the sort well known in the art) provided, so as to permit the surgeon to alter the curvature of arc 45, whereby to facilitate advancement of arthroscopic debridement template 15 to the surgical site and/or to allow the curvature of arc 45 to be modified in situ so as to better guide the surgeon in the desired debridement of the bone. In this form of the invention, the additional control means 48 (e.g., control wires, push rods, etc.) which are provided on the apparatus so as to permit the surgeon to alter the curvature of arc 45 are preferably connected to a handle or trigger (not shown) disposed at the proximal end of shaft 20 for appropriate actuation by the surgeon.

Additionally, arthroscopic debridement template 15 may be removable from shaft 20, so that the surgeon can exchange one arthroscopic debridement template 15 having a given arc 45 for a different arthroscopic debridement template 15 having a different arc 45. In this form of the invention, arthroscopic debridement template 15 may be reusable or disposable. Furthermore, if desired, arthroscopic debridement template 15 may incorporate a light source 49 for better visualization of the debridement site.

Figure 20A:
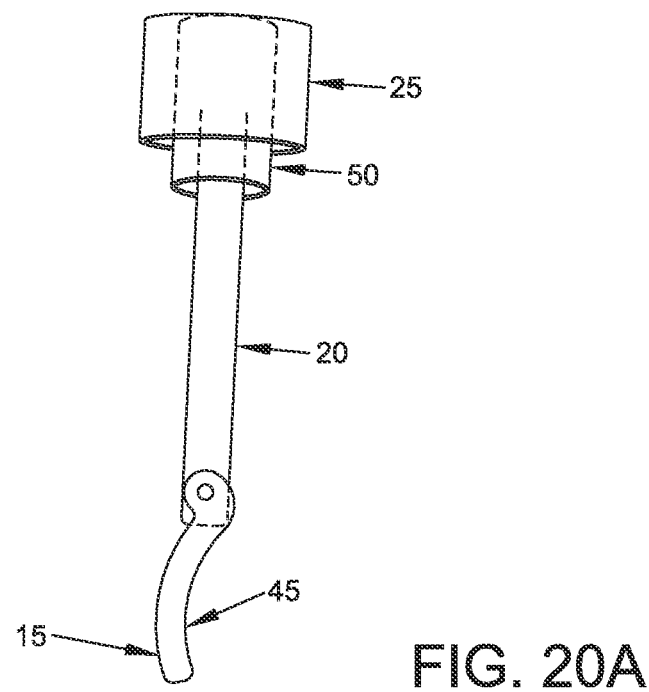
FIGS. 20A and 20B are schematic views of another arthroscopic debridement template formed in accordance with the present invention.
Figure 20B:
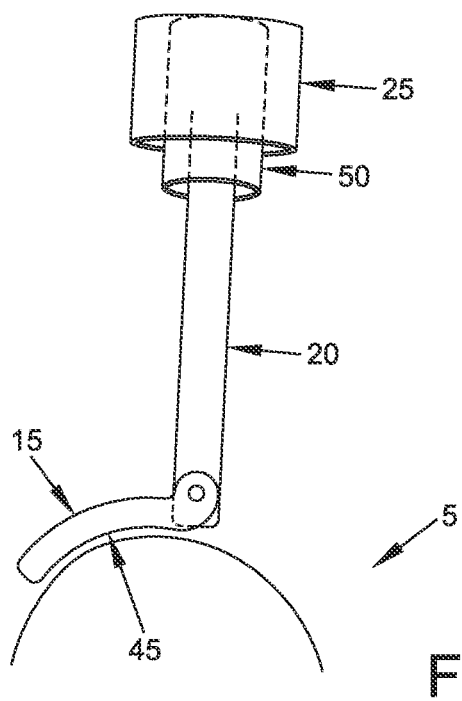
Figure 21:
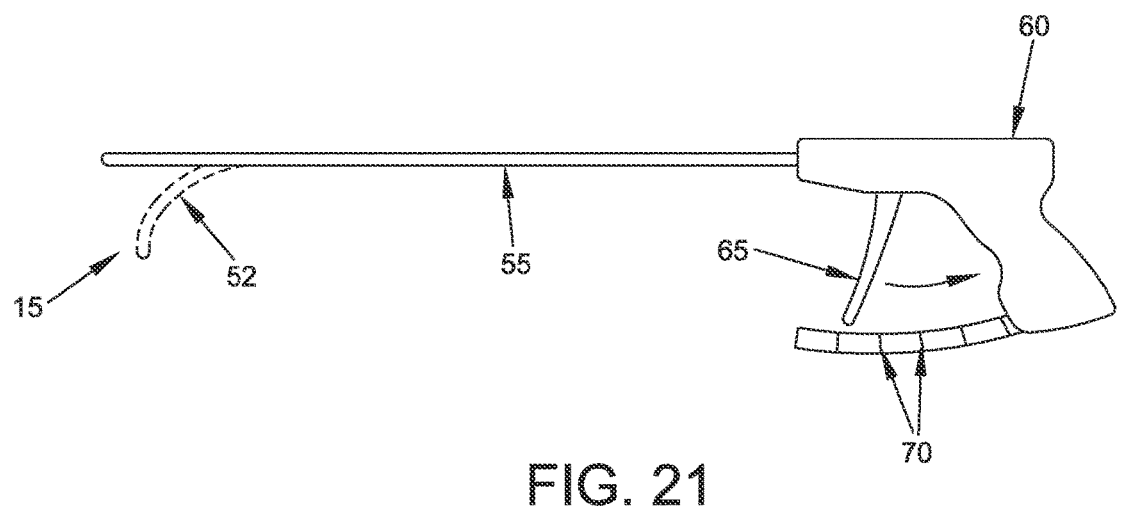
FIGS. 21-24 are schematic views of another arthroscopic debridement template formed in accordance with the present invention.
Figure 22A:
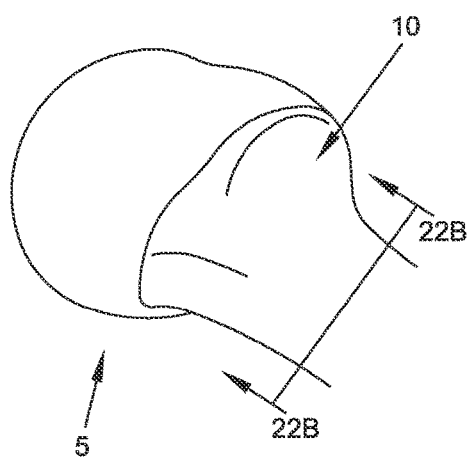
Figure 22B:
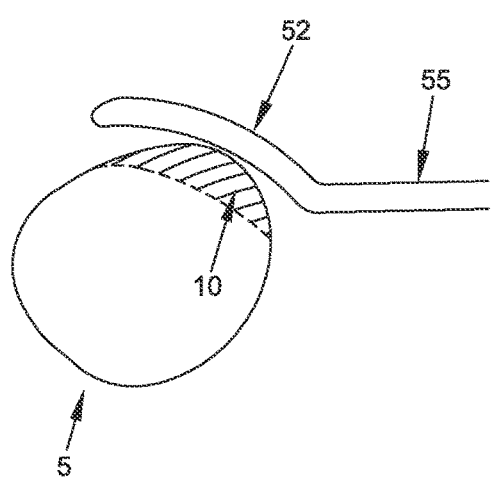
Figure 23A:
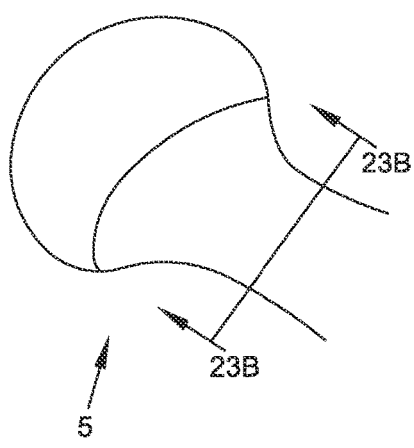
Figure 23B:
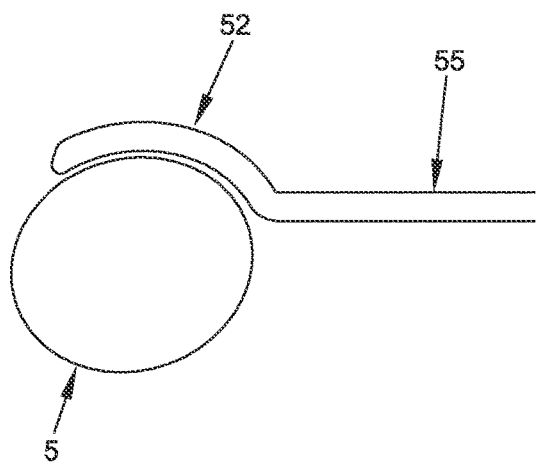
Figure 24:
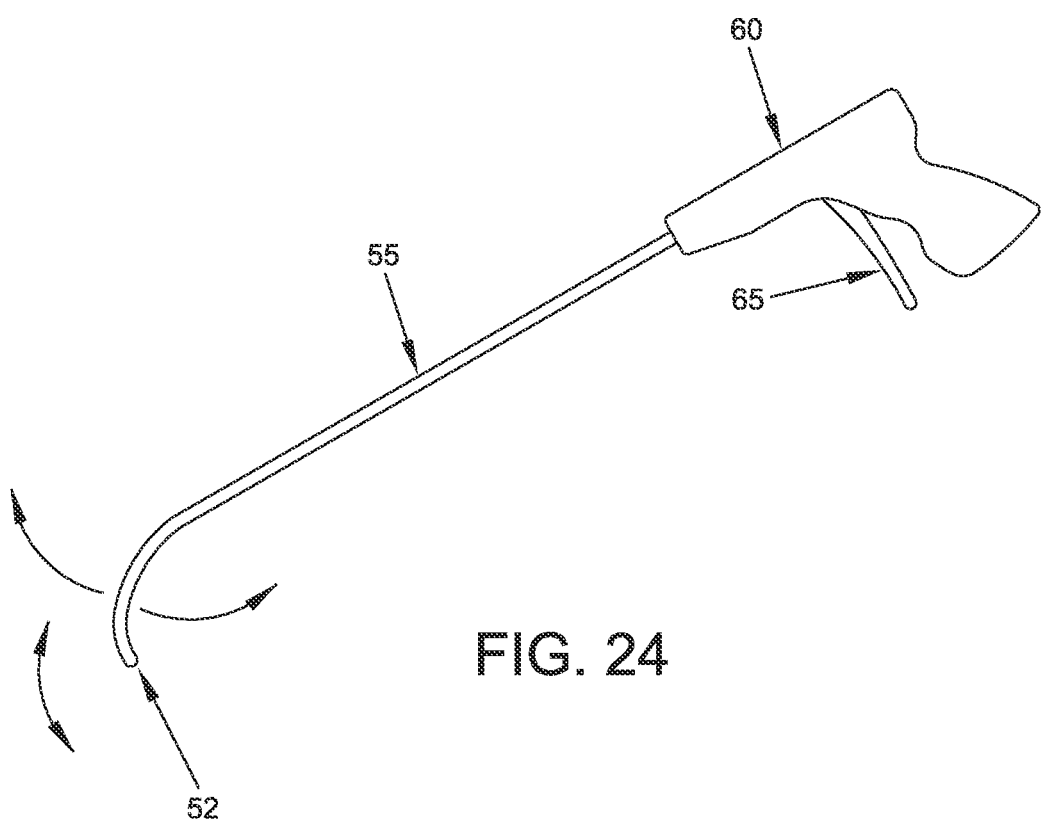
Figure 25:
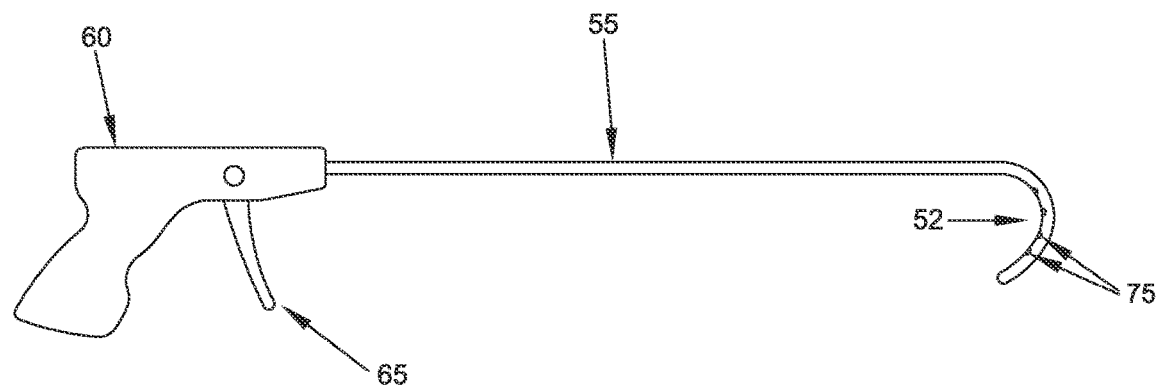
FIGS. 25-28 are schematic views of another arthroscopic debridement template formed in accordance with the present invention.
Figure 26:
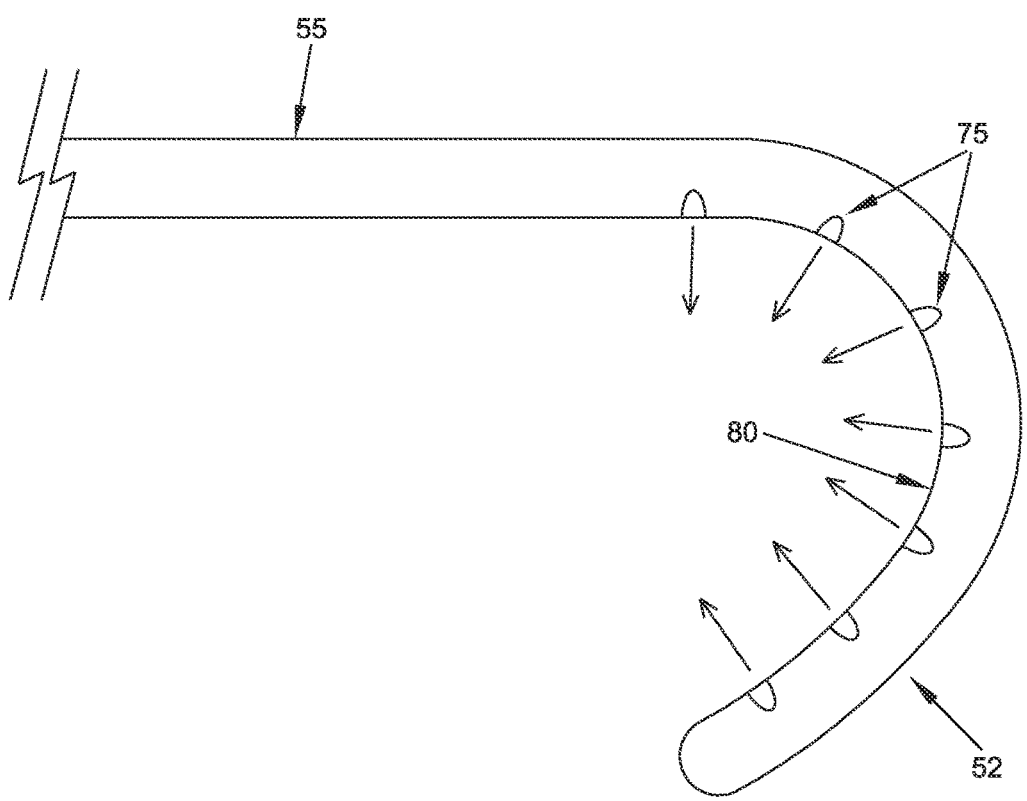

In another form of the present invention, and looking now at FIGS. 20A and 20B, the arthroscopic debridement template 15 is generally similar to the arthroscopic debridement template 15 shown in FIG. 20, except that arthroscopic debridement template 15 is formed with a reduced profile so as to facilitate delivery to, and removal from, the arthroscopic site. In this form of the invention, when arthroscopic debridement template 15 is passed through an arthroscopic access cannula 25, arthroscopic debridement template 15 is substantially longitudinally aligned with shaft 20 (FIG. 20A). Once arthroscopic debridement template 15 has been passed through the arthroscopic access cannula, the arthroscopic debridement template 15 may be pivoted so as to align its arc 45 with the target bone surface (FIG. 20B).

Arthroscopic debridement template 15 may also be telescopically housed in an inserter tube 50 such that when arthroscopic debridement template 15 is passed to and from the joint (e.g., through arthroscopic access cannula 25), arthroscopic debridement template 15 is housed within inserter tube 50, and when arthroscopic debridement template 15 is in the joint, arthroscopic debridement template 15 is extended out of inserter tube 50.

In another form of the present invention, and looking now at FIGS. 21, 22A, 22B, 23A, 23B and 24, arthroscopic debridement template 15 may comprise a flexible tip 52, formed integral with, or attached to, the distal end of a substantially rigid shaft 55. In this form of the invention, a handle 60 is disposed on the proximal end of shaft 55 so as to allow the surgeon to adjust the curvature of flexible tip 52 by pulling/pushing a trigger 65 mounted on handle 60 (e.g., which operates control wires, push rods, etc. of the sort well known in the art, not shown, which connect flexible tip 52 to trigger 65). In this way the curvature of flexible tip 52 can be adjusted so as to reflect the desired bone geometry. In one preferred form of the invention, handle 60 and trigger 65 incorporate a ratchet mechanism such that when the desired curvature is reached, the trigger can be released and the apparatus remains locked in position, with flexible tip 52 in the desired position. In this form of the invention, a release is provided so as to allow the apparatus to return to its starting configuration when desired. Such ratchet mechanisms and releases are well known in the art of handles and triggers. Handle 60 may further include markings 70 to indicate the degree of curvature of flexible tip 52 when trigger 65 is actuated. See FIG. 21.

During the debridement procedure, and looking now at FIGS. 22A, 22B, 23A and 23B, the shaft 55 carrying flexible tip 52 is advanced through an arthroscopic access cannula to the impingement site 10 (e.g., at the femoral neck, at the femoral head, at the transition between the femoral neck and the femoral head, etc.), and then the surgeon adjusts the degree of curvature of flexible tip 52 (using trigger 65 on handle 60) so that flexible tip 52 forms an arc reflecting the desired bone geometry. The thus-configured flexible tip 52 may then be positioned adjacent to the impinging bone 10 and used by the surgeon to guide the desired bone debridement.

In one preferred form of the invention, flexible tip 52 is able to articulate in different directions (FIG. 24) relative to the longitudinal axis of shaft 55 (e.g., up, down, left, right, etc.) so as to provide the surgeon with more options for approaching the impingement site—such a construction can be particularly desirable in a joint where the angle of approach is restricted and/or in a "tight" joint where workspace is limited (e.g., inside the hip joint).

Optical Arthroscopic Debridement Templates

In another form of the present invention, and looking now at FIGS. 25-28, arthroscopic debridement template 15 may comprise the flexible tip 52 construction shown in FIGS. 21-24 and may further include one or more lights 75 disposed in and/or along the length of flexible tip 52 so as to aid the surgeon in determining where and how much bone is to be debrided. More particularly, in this form of the invention, and looking now at FIG. 26, one or more lights 75 are directed toward the surface of the bone from the inner surface 80 of the arc formed by flexible tip 52. The light(s) 75 may be recessed within inner surface 80 of flexible tip 52 and/or light(s) 75 may be flush with inner surface 80 of flexible tip 52. In one form of the invention, light(s) 75 may be active elements (e.g., LEDs) disposed at flexible tip 52. In another form of the invention, light(s) 75 may be the distal end(s) of light fiber(s) extending through shaft 55 and flexible tip 52, with the source of the light (not shown) disposed in handle 60 of the apparatus, such that the light generated at the light source is transmitted to the distal end of shaft 55 by the light fiber(s).

Figure 27:
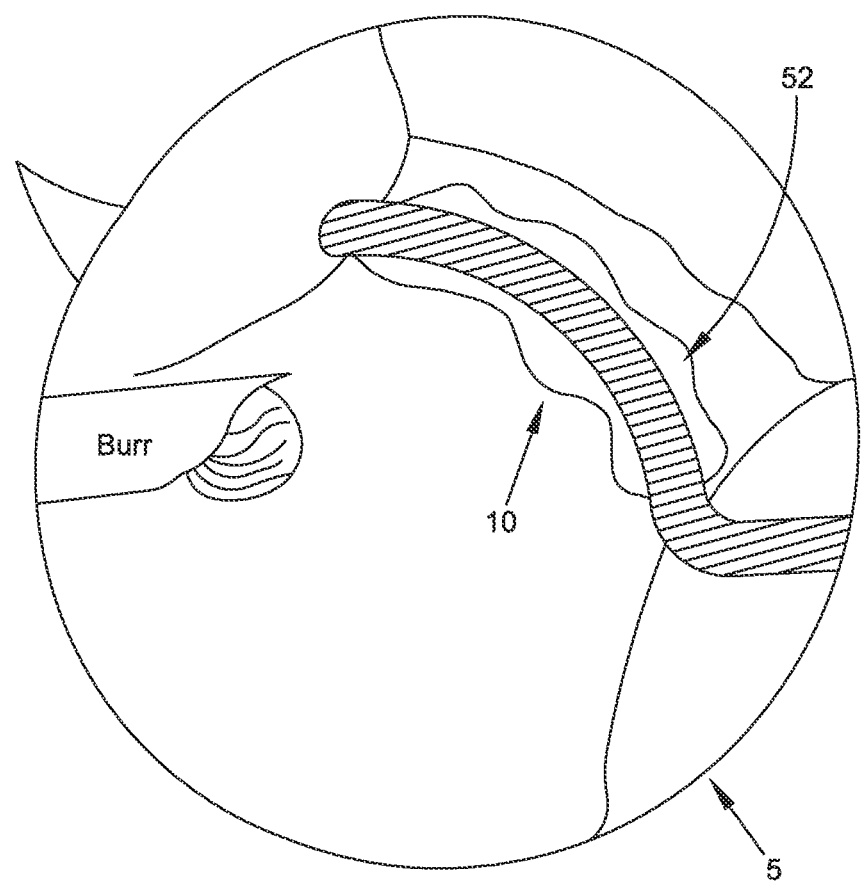
Figure 28:
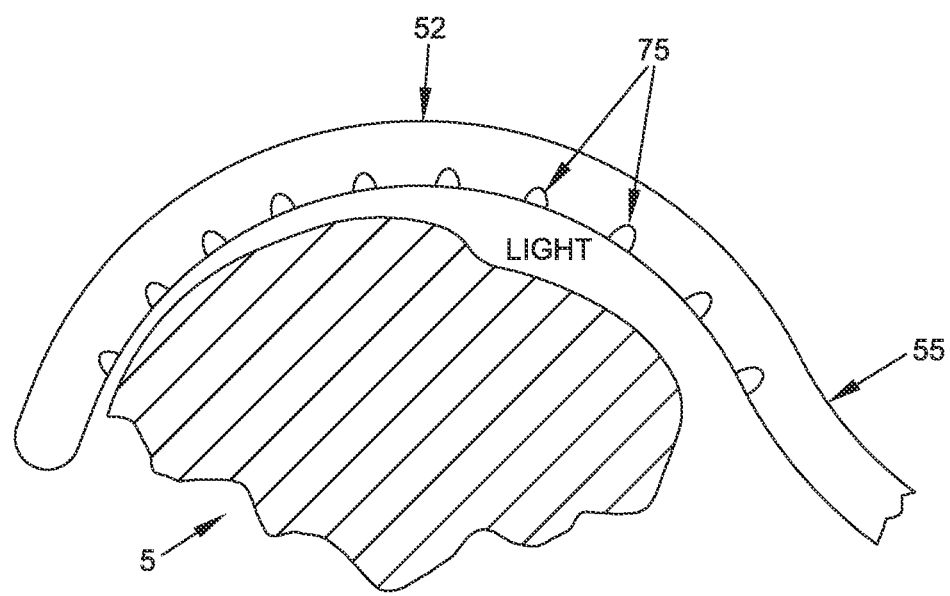
Figure 29:
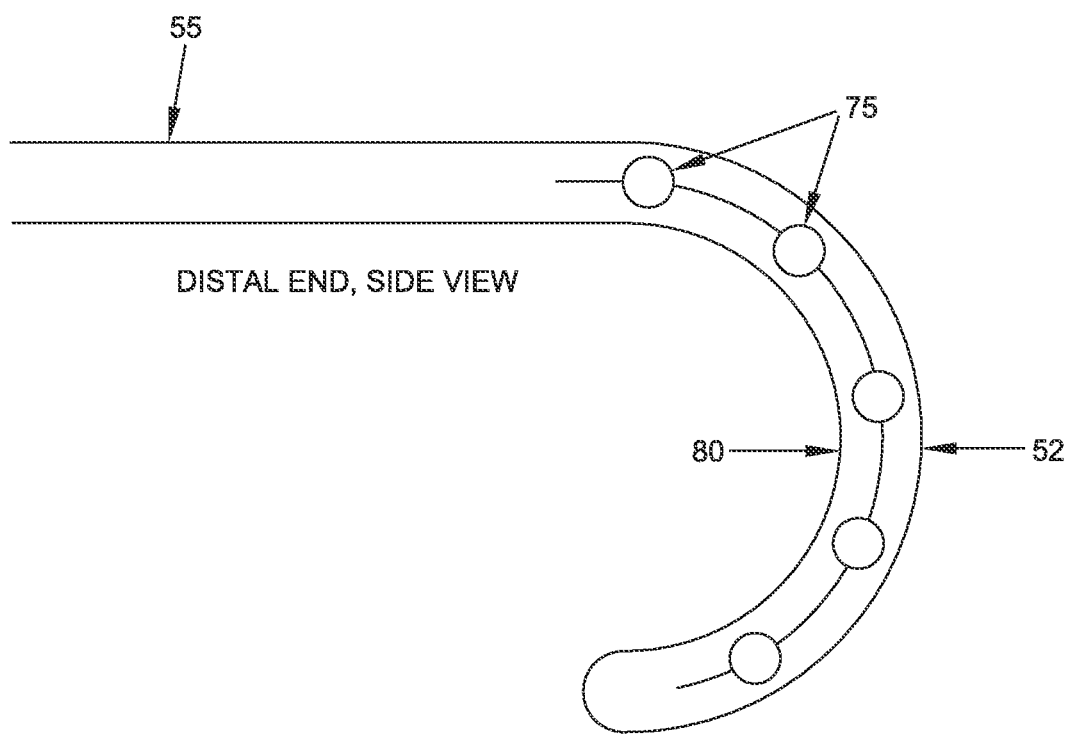
FIGS. 29-32 are schematic views of another arthroscopic debridement template formed in accordance with the present invention.
Figure 30:
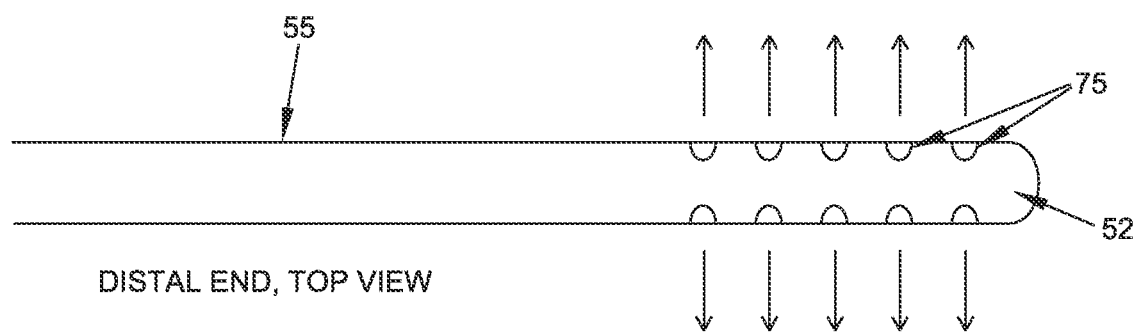
Figure 31:
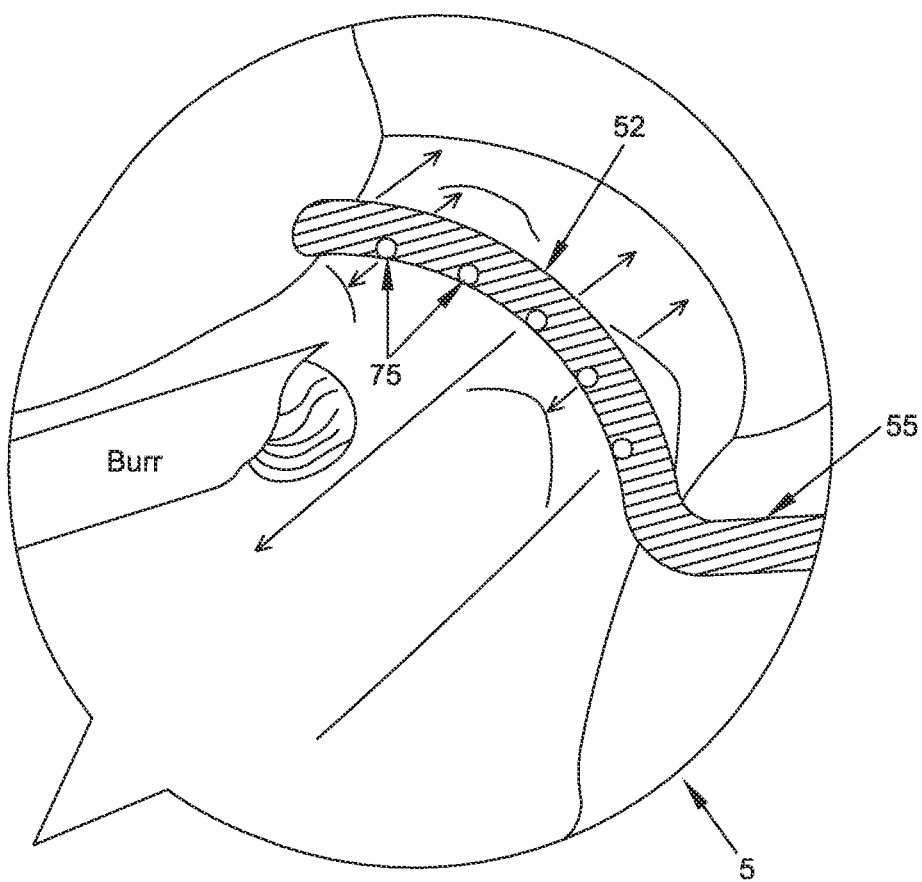
Figure 32:
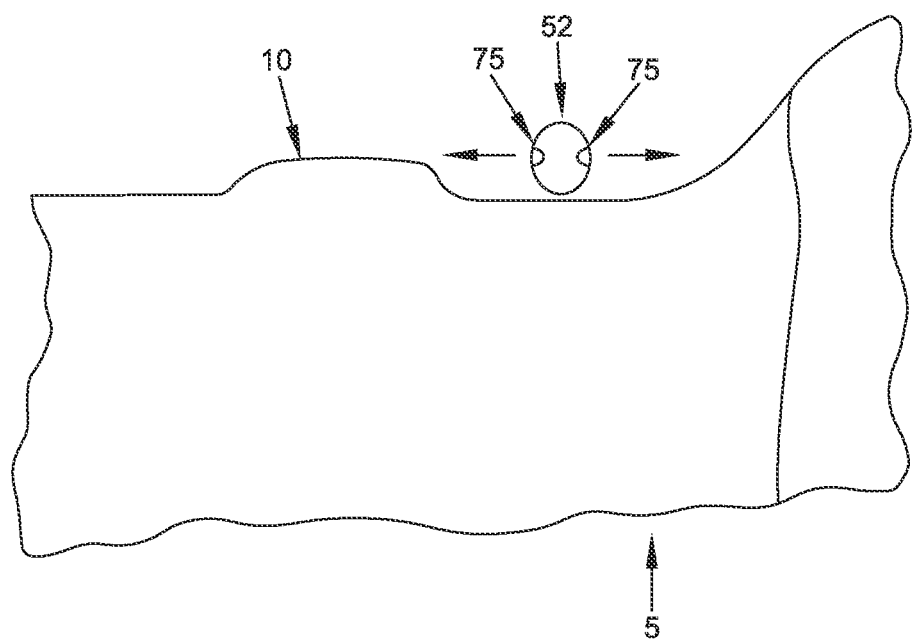

During the debridement procedure, and looking now at FIGS. 27 and 28, the shaft 55 carrying flexible tip 52 is advanced by the surgeon through an arthroscopic access cannula to the impingement site 10 (e.g., at the femoral neck, at the femoral head, at the transition between the femoral neck and the femoral head, etc.), and then the surgeon adjusts the curvature of flexible tip 52 (e.g., using trigger 65) so that the curvature of flexible tip 52 properly reflects the desired bone geometry. The surgeon then advances flexible tip 52 so that flexible tip 52 is disposed adjacent to the bone which is to be debrided, with the inner surface 80 of flexible tip 52 forming an arc which represents the desired geometry for the bone. When light(s) 75 are activated, light is emitted from light(s) 75 in the arc of flexible tip 52 and is directed toward the surface of the bone. Where flexible tip 52 is flush with the surface of the bone, no light will be seen, and where flexible tip 52 is spaced from the bone, light will be visible (i.e., due to the light reflecting off the bone and visible through the space formed between flexible tip 52 and the bone), thereby assisting the surgeon in identifying how the curvature of the native bone differs from the desired geometry and providing guidance as to how much bone is to be debrided.

In another form of the present invention, and looking now at FIGS. 29-32, flexible tip 52 is formed so that the light from light(s) 75 is emitted perpendicular to the radius of curvature of the arc formed by a bent flexible tip 52 (i.e., at a 90° angle to the inner surface 80 of the arc). In this form of the invention, when flexible tip 52 has been appropriately configured and its inner surface 80 is pressed up against the surface of the bone which is to be debrided, the light from light(s) 75 travels along the surface of the bone (i.e., sideways from flexible tip 52). Where there is a spur or "bump" in the bone, indicative of an impingement site, passage of the light from light(s) 75 is blocked, thereby indicating a portion of the bone to be debrided. See FIGS. 31 and 32. It should be appreciated that the light may be emitted from one or both sides of flexible tip 52, as desired.

Figure 33:
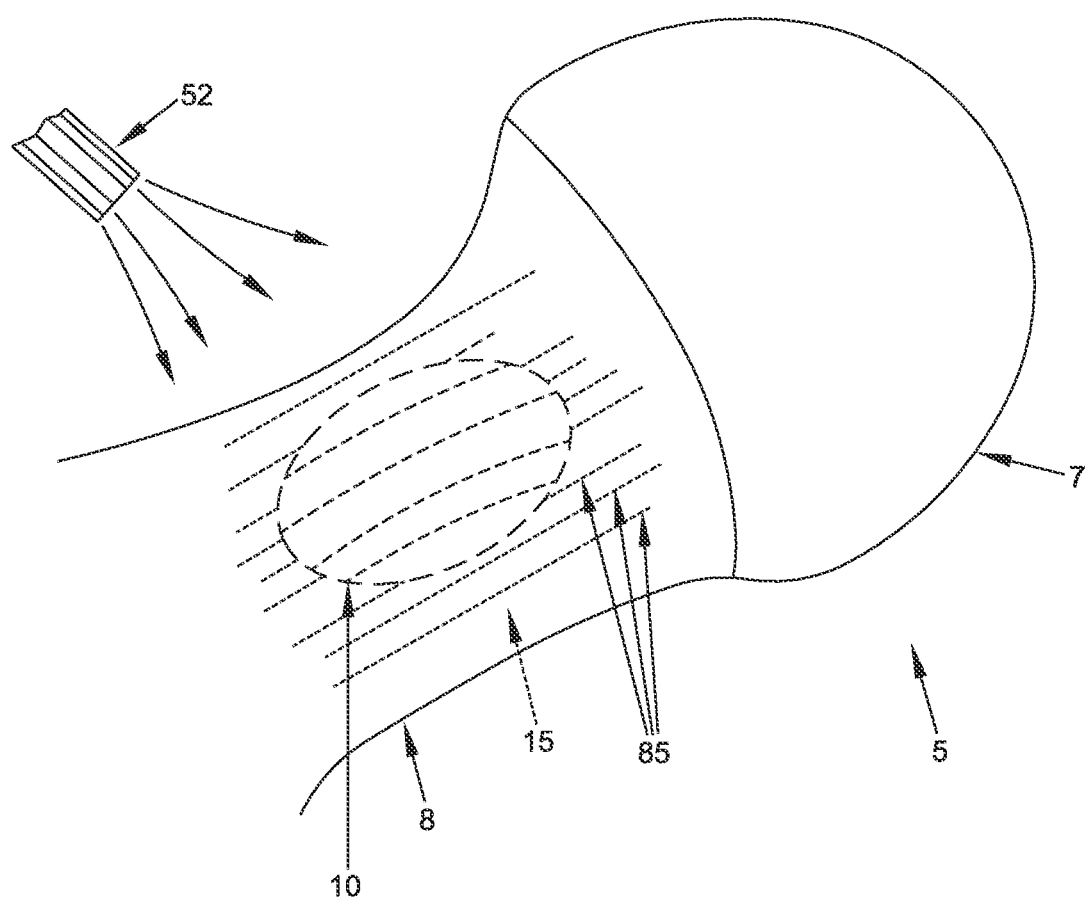
FIG. 33 is a schematic view of an arthroscopic debridement template formed in accordance with the present invention.

In another form of the present invention, and looking now at FIG. 33, arthroscopic debridement template 15 is a light pattern projected onto the surface of the bone. More particularly, in this form of the invention, the apparatus (e.g., flexible tip 52) is constructed so as to project a light pattern onto the surface of the bone so as to assist the surgeon in locating the impingement site(s) 10 to be debrided. More particularly, in this form of the invention, a light pattern 85 (e.g., a grid, parallel lines, dots, squiggles, concentric circles, etc.) is projected onto the surface of the bone. Where the topography of the surface of the bone varies (e.g., where the surface of the bone is raised at a point of impingement), the light pattern 85 is modified by the irregular topography of the bone. By way of example but not limitation, when the light pattern 85 is directed onto a portion of the bone including a bony protrusion (e.g., a bone "spur") such as that which may cause impingement, the projected light pattern 85 is modified by the bump (e.g., such as by going from linear to non-linear, in the manner shown in FIG. 33), indicating to the surgeon the location of the bony protrusion.

Figure 34:
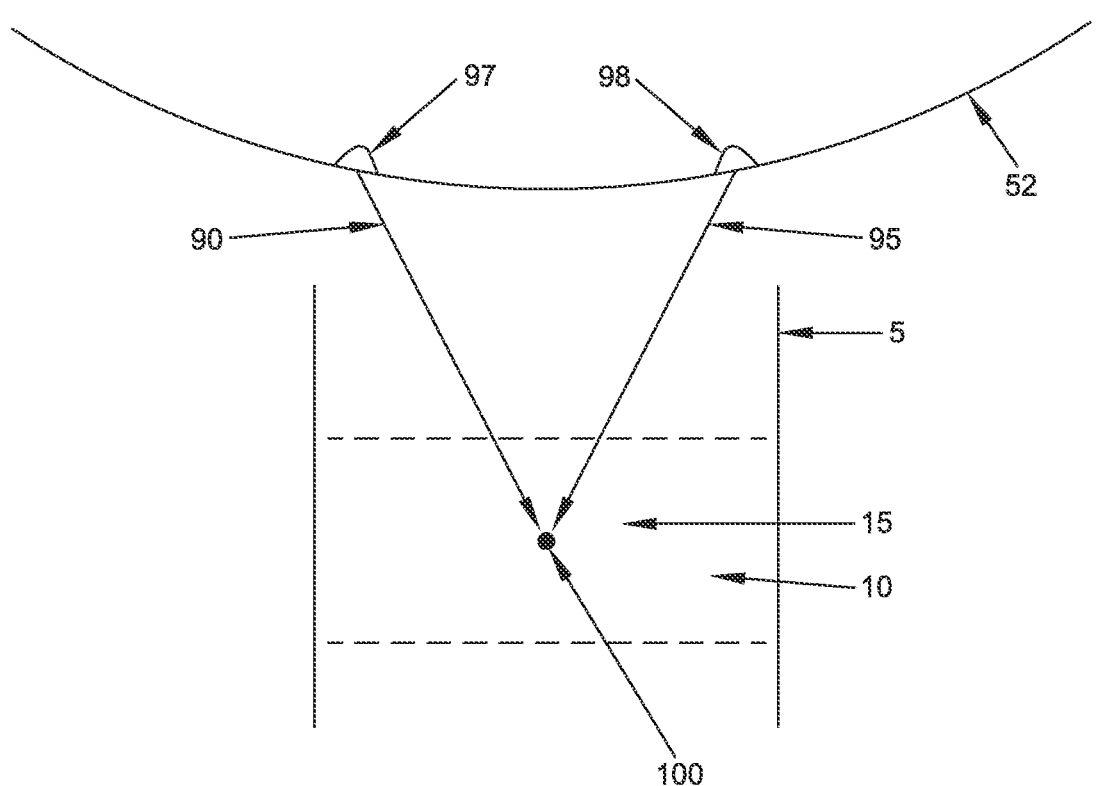
FIGS. 34-36 are schematic views of another arthroscopic debridement template formed in accordance with the present invention.
Figure 35:
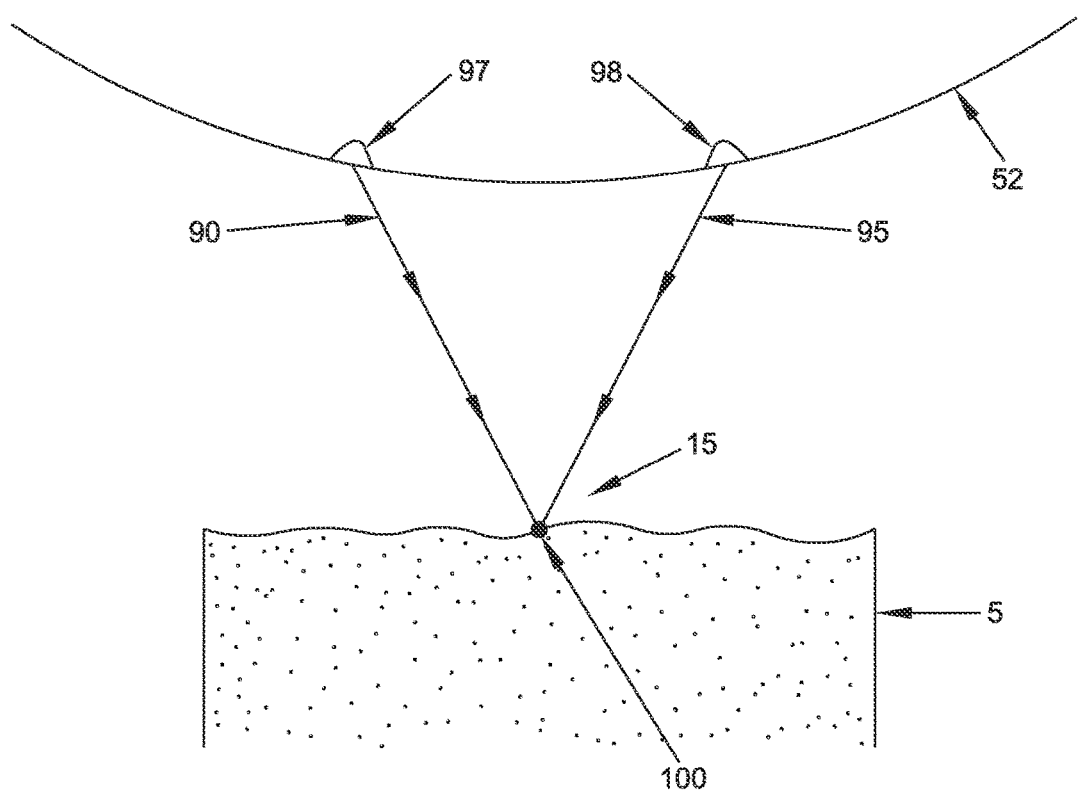
Figure 36:
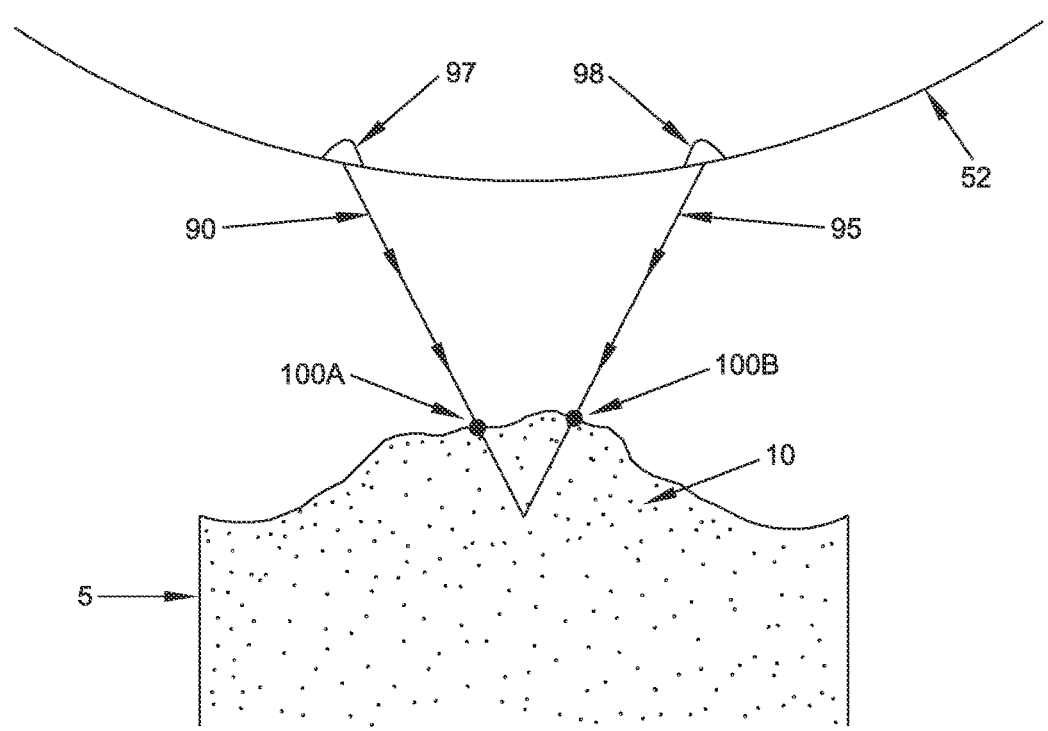

If desired, and looking now at FIGS. 34-36, arthroscopic debridgement template 15 may comprise a light pattern formed by two converging beams of light 90, 95 generated by light sources 97, 98 (e.g., light sources carried by flexible tip 52). In this form of the invention, the two converging beams of light 90, 95 are directed onto the surface of the bone, with the two beams of light set so that they are directed onto a common point 100 (i.e., the "focal point") on the surface of the bone. The focal point 100 is selected so that it is set at a predetermined distance from the sources 97, 98 of the two converging beams of light 90, 95. As a result, when the arthroscopic debridement template 15 is positioned next to the bone so that the two converging beams of light 90, 95 form a single point 100 (FIGS. 34 and 35), and the arthroscopic debridement template 15 is thereafter moved laterally along the bone, the converging beams of light 90, 95 will remain "in focus" (i.e., forming a single point of light 100) as long as the surface of the bone is uniform, and the converging beams of light 90, 95 will move "out of focus" (e.g., into a pair of separated points 100A, 100B, in the manner shown in FIG. 36) at those points where the surface of the bone varies in elevation (e.g., at bony protrusions or bumps which may cause impingement). In this way, arthroscopic debridement template 15 serves to identify impingement points 10 to the surgeon.

Figure 37:
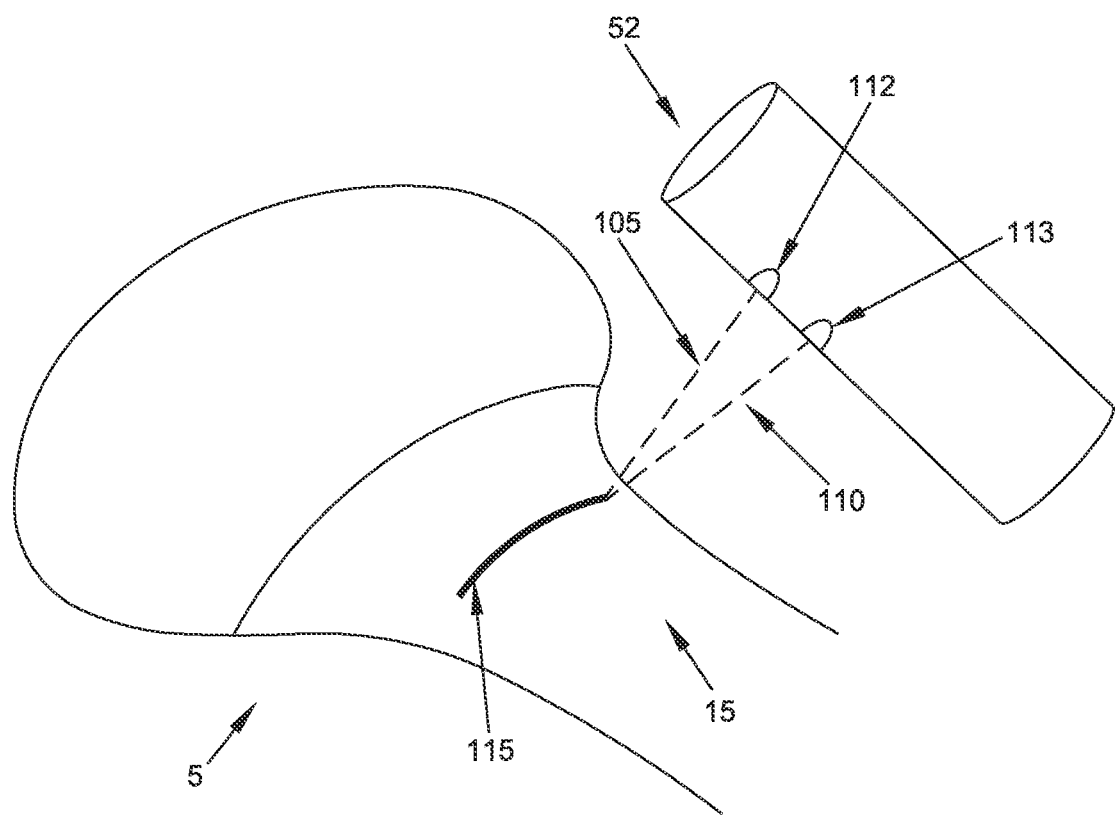
FIGS. 37 and 38 are schematic views of another arthroscopic debridement template formed in accordance with the present invention.
Figure 38:
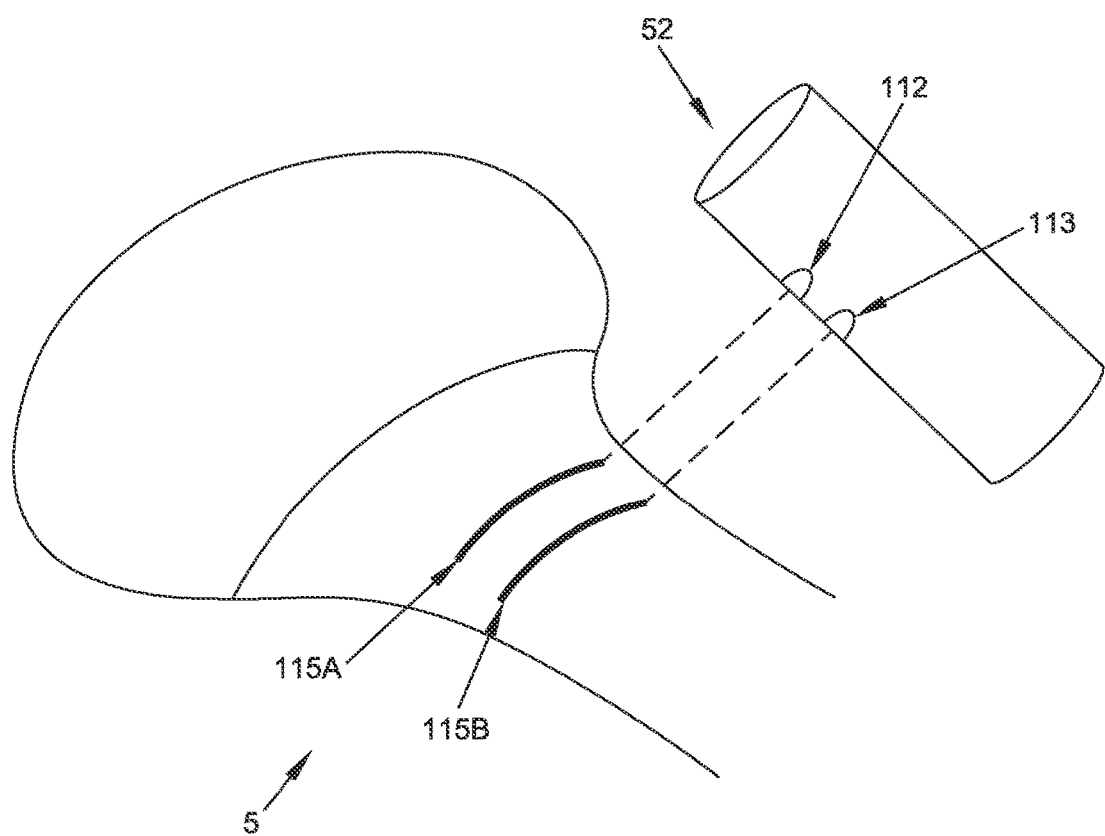

In another form of the present invention, and looking now at FIGS. 37 and 38, arthroscopic debridement template 15 may comprise a light pattern formed by two converging lines of light 105, 110 generated by light sources 112, 113 (e.g., light sources carried by flexible tip 52). In this form of the invention, the two converging lines of light 105, 110 are directed onto the surface of the bone, with the two lines of light 105, 110 set so that they are directed onto a common location 115 (i.e., the "focal point") on the surface of the bone. The focal point 115 is selected so that it is set at a predetermined distance from the sources 112, 113 of the two converging lines of light 105, 110. As a result, when arthroscopic debridement template 15 is positioned next to the bone so that the two converging lines of light 105, 110 form a single line 115 (FIG. 37), and the arthroscopic debridement template 15 is thereafter moved laterally along the bone, the converging lines of light 105, 110 will remain "in focus" (i.e., forming a single line of light 115) as long as the surface of the bone is uniform, and the converging lines of light 105, 110 will move "out of focus" (e.g., into a pair of separated lines 115A, 115B, in the manner shown in FIG. 38) at those points where the surface of the bone varies in elevation (e.g., at bony protrusions or bumps which may cause impingement). In other words, with this form of the present invention, arthroscopic debridement template 15 is configured so as to display a single line of light 115 (FIG. 37) when arthroscopic debridement template 15 is positioned at the "focal distance" from the bone, and to display a pair of lines of light 115A, 115B (FIG. 38) when arthroscopic debridement template 15 is not positioned at the "focal distance" from the bone, whereby to provide the surgeon with a means for detecting bone protrusions.

Figure 39A:
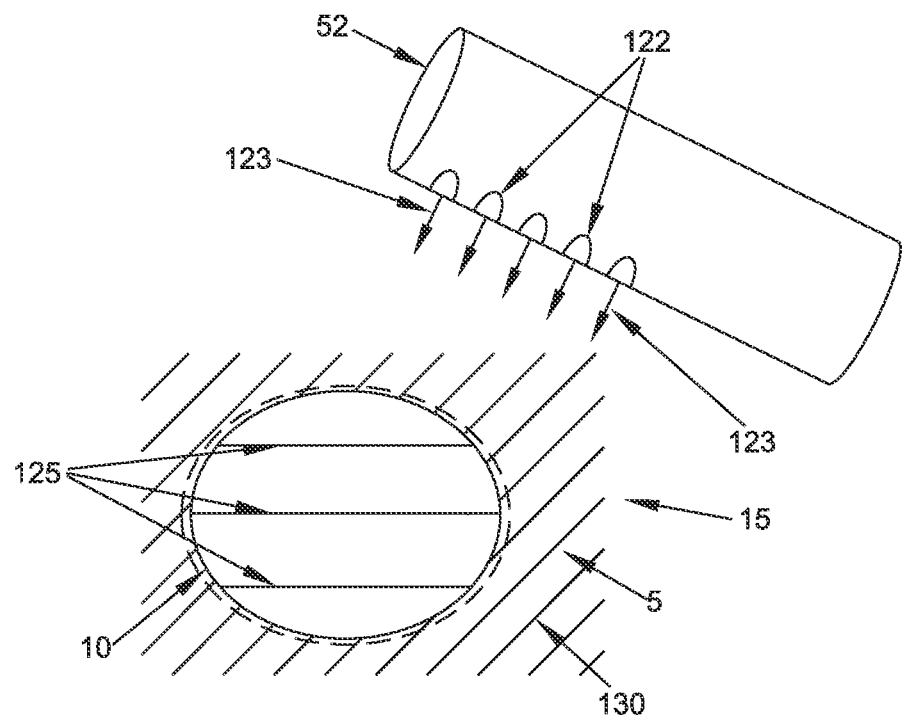
FIGS. 39A and 39B are schematic views of another arthroscopic debridement template formed in accordance with the present invention.
Figure 39B:
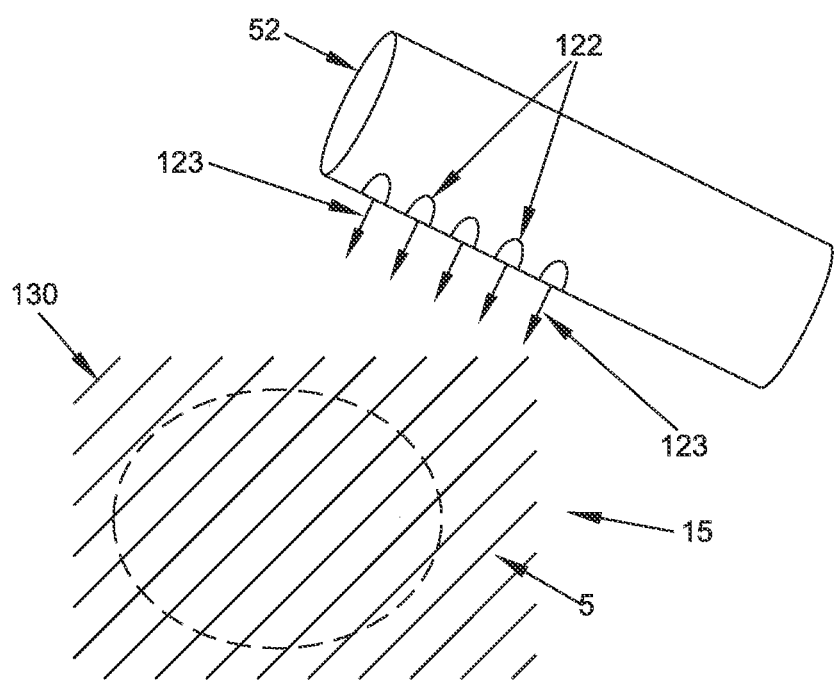
Figure 39:
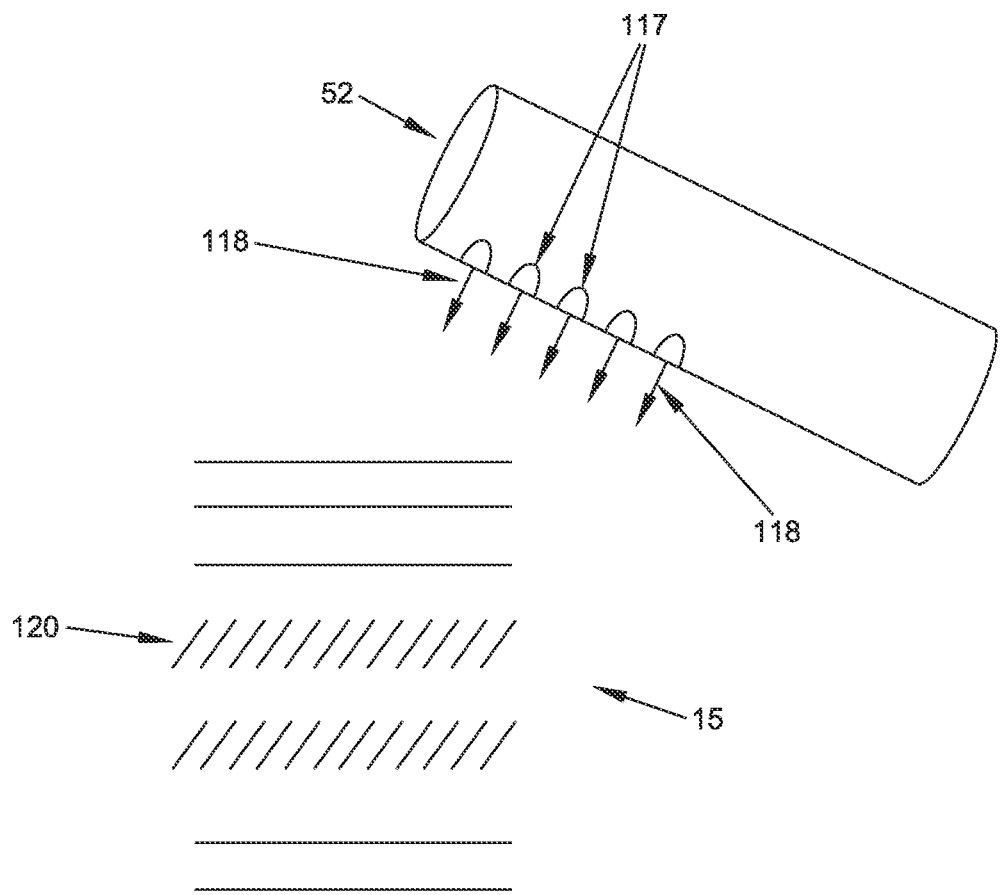
FIG. 39 is a schematic view of an arthroscopic debridement template formed in accordance with the present invention.
Figure 40:
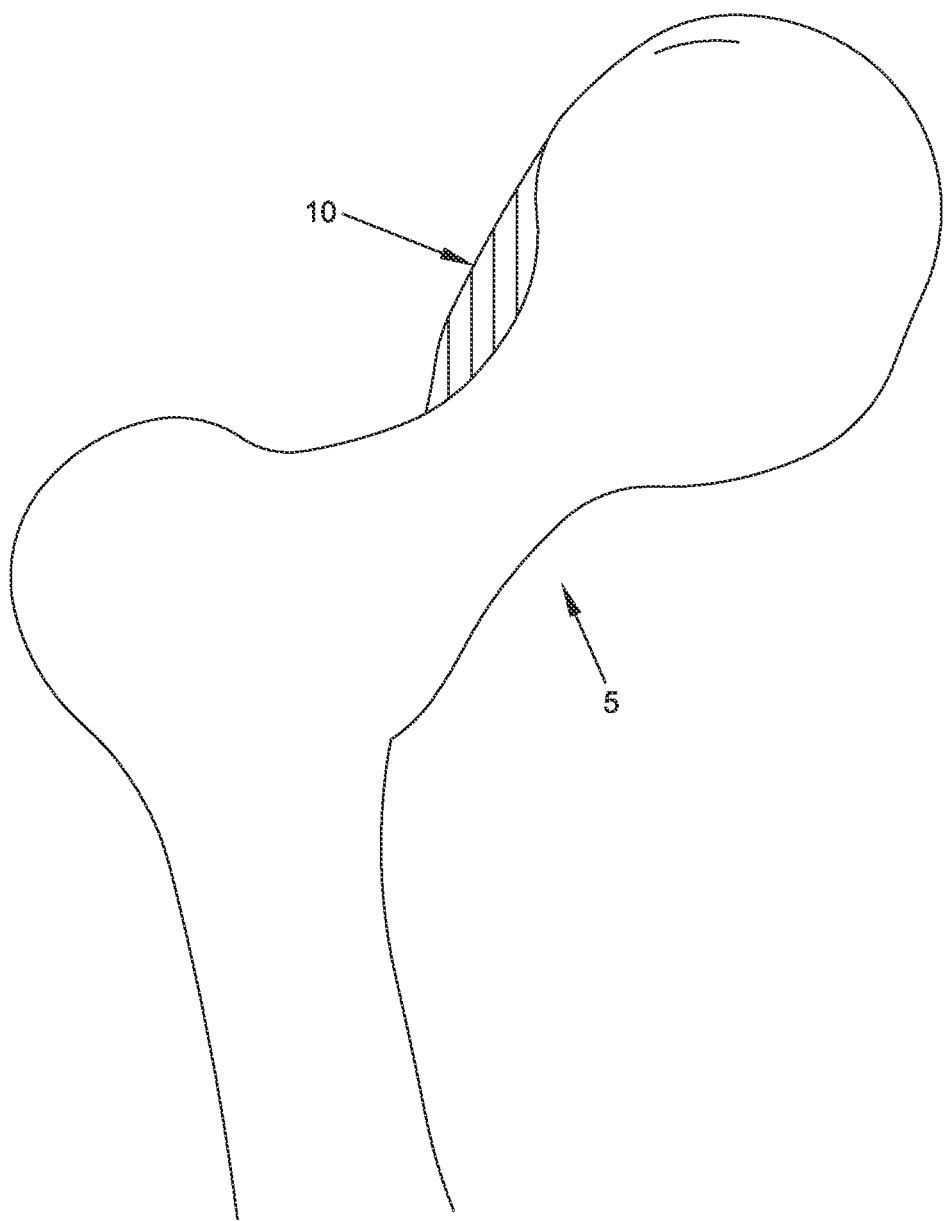
FIGS. 40-43 are schematic views of another arthroscopic debridement template formed in accordance with the present invention.
Figure 41:
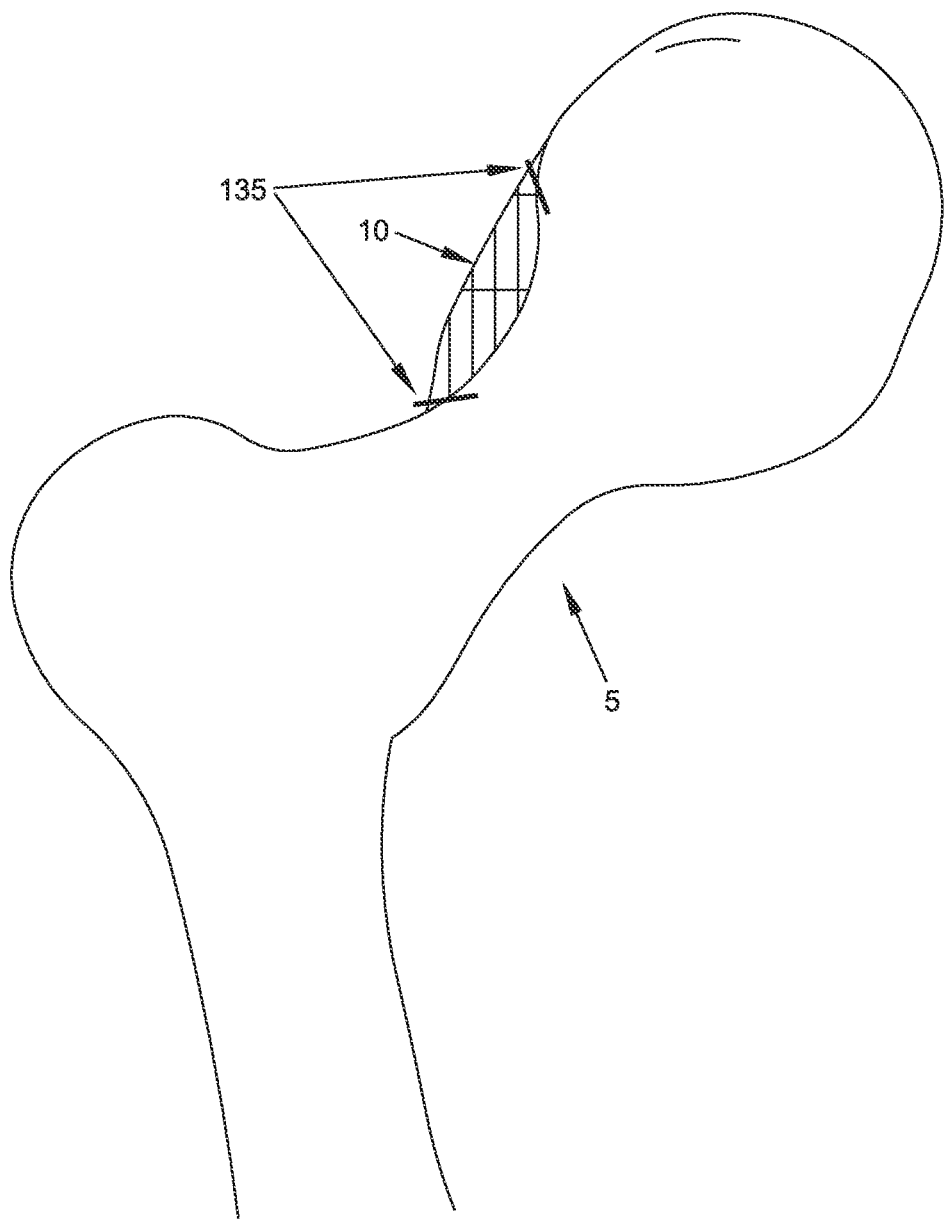
Figure 42:
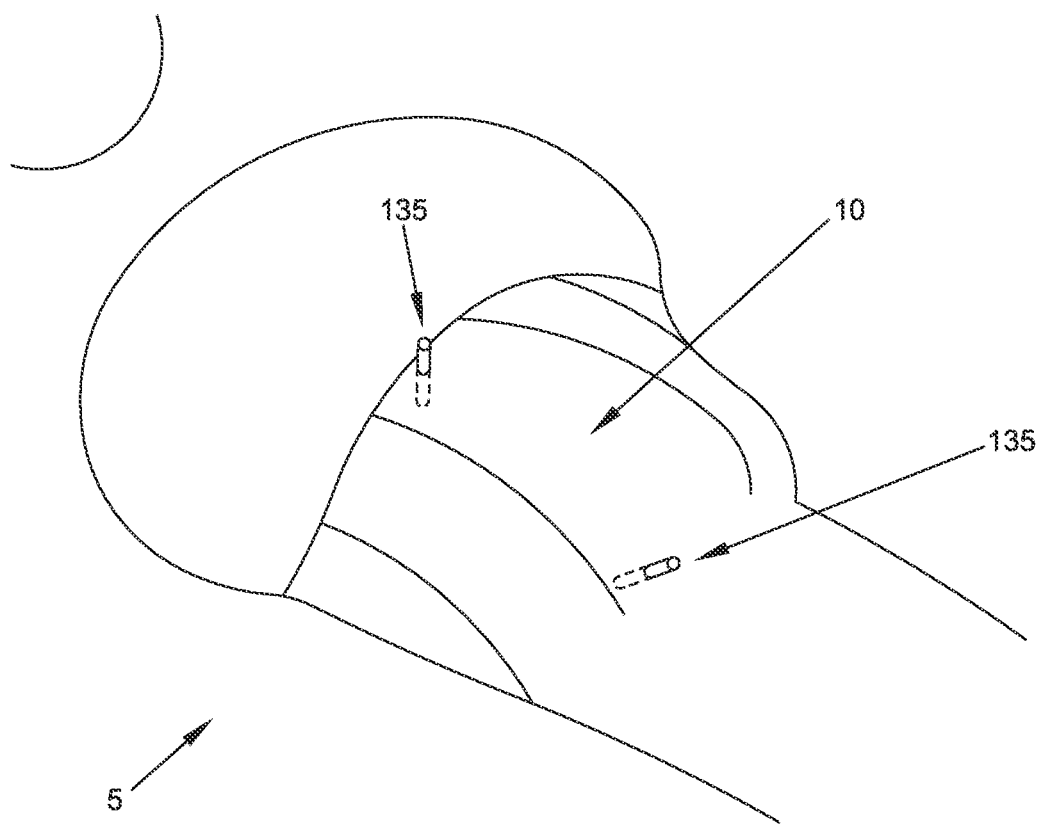
Figure 43:
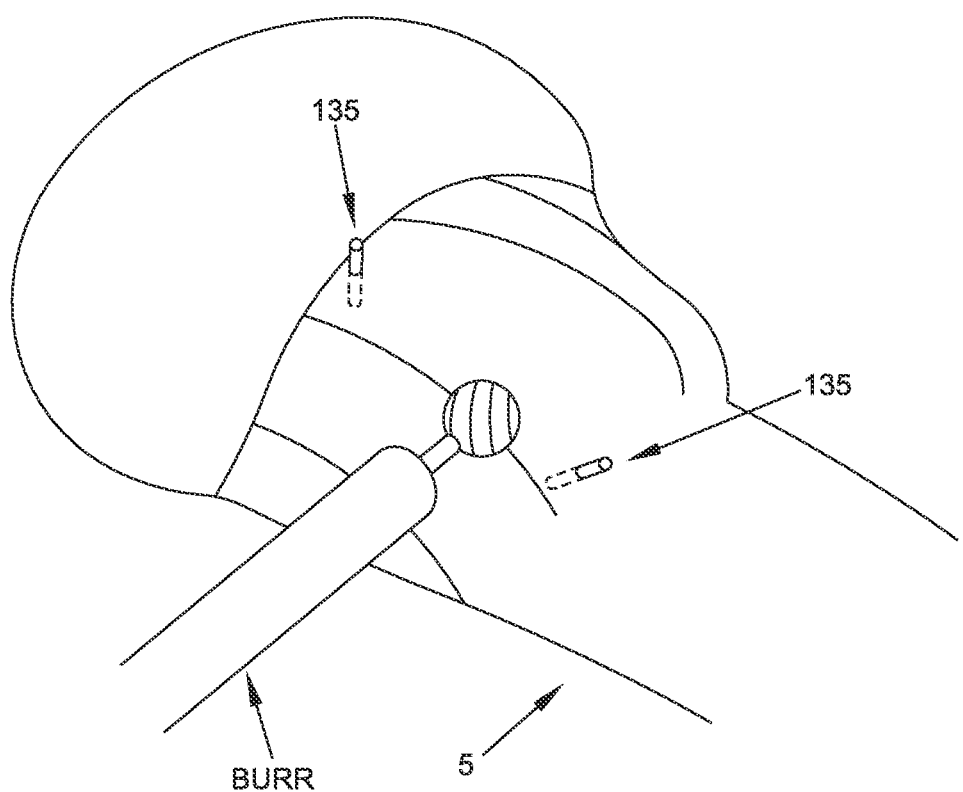

And in another form of the present invention, and looking now at FIG. 39, arthroscopic debridement template 15 may comprise light sources 117 (e.g., light sources carried by flexible tip 52) which generate a plurality of beams of light 118, wherein the beams of light 118 are configured so as to create an interference pattern 120 when they encounter a variation in the elevation of the bone (e.g., a bony protrusion), thereby providing the surgeon with a visual cue for guiding the debridement process.

In another form of the present invention, and looking now at FIGS. 39A and 39B, arthroscopic debridement template 15 may comprise light sources 122 (e.g., light sources carried by flexible tip 52) which generate a plurality of beams of light 123, wherein the beams of light 123 are configured so as to form discrete patterns 125 (e.g., lines, points, etc.) on the impinging bone surface which is to be debrided and diffuse areas of light 130 on the bone surrounding the impinging bone surface (FIG. 39A), and diffuse areas of light 130 across the entire bone surface after appropriate bone debridement (FIG. 39B).

In another embodiment of the present invention, and looking now at FIGS. 40-43, arthroscopic debridement template 15 may comprise markers 135 which are used to delineate the perimeter of a bony protrusion 10 which is to be debrided and/or to mark the depth to which the bony protrusion needs to be debrided. Markers 135 may be formed out of a biocompatible material such as metal (e.g., stainless steel), plastic, etc. Markers 135 may comprise a color, surface texture, shape and/or reflectivity which makes them easily identifiable under endoscopic visualization. Markers 135 may be made out of a material that is visible under X-ray imaging, such as a material having a higher radiodensity than bone (e.g., metal, plastic filled with $BaSO_4$, etc.) or a material having a lower radiodensity than bone (e.g., plastic). Markers 135 may be made out of a material which is visible under other imaging means (e.g., MRI, ultrasound, etc.). By way of example but not limitation, and looking now at FIG. 40, a bony protrusion 10 is first identified by the surgeon (e.g., by way of one of the foregoing approaches, such as by using a mechanical arthroscopic debridement template 15 or another light-based arthroscopic debridement template 15, etc.) and targeted for debridement. Next, one or more markers 135 are implanted into the bone (see, for example, FIGS. 41 and 42), with the distal end of the marker 135 preferably being set at the depth desired for the bone surface after debridement in that region of the bony protrusion. Debridement can then proceed (see, for example, FIG. 43) so as to remove the bony protrusion 10, with the surgeon using the one or more markers 135 as a guide for indicating the location and/or depth of the bone which is to be removed. The surgeon may consult imaging means (e.g., X-ray, MRI, ultrasound, etc.) or visualization means (e.g., an endoscopic camera, etc.) as necessary during the procedure so as to confirm how much bone needs to be debrided in order to achieve the desired bone geometry.

Marker(s) 135 are removed from the bone at or near the completion of the bone debridement procedure.

In another form of the present invention, one or more markers 135 are placed within the bone which is to be removed (i.e., within the bone protrusion). Markers 135 extend to a depth which is reflective of the amount of bone which is to be removed. The surgeon then uses the markers 135 as a guide for indicating the location and/or depth of the bone which is to be removed. In this form of the invention, the one or more markers 135 are removed from the patient prior to completion of the bone debridement procedure, such that the bone in which they resided can be fully debrided.

In one form of the present invention, a hole is first drilled into the bone and then the marker 135 is placed within the hole. In another form of the present invention, the marker 135 is driven directly into the bone (e.g., with a mallet) without forming a hole first. If desired, marker 135 may comprise surface features (e.g., screw threads, barbs, etc.) for enhancing engagement with the bone.

Of course, it should be appreciated that, if desired, marker(s) 135 may be utilized only for marking the perimeter of the bony protrusion which is to be removed, and the depth of bone debridement may be determined by other means (e.g., by use of one of the foregoing approaches). It should also be appreciated that marker(s) 135 may be utilized only for showing the depth of the bone debridement and the perimeter of the bone debridement may be indicated by other means.

Arthroscopic Debridement Templates Incorporating a Bone Cutting Element

Figure 44:
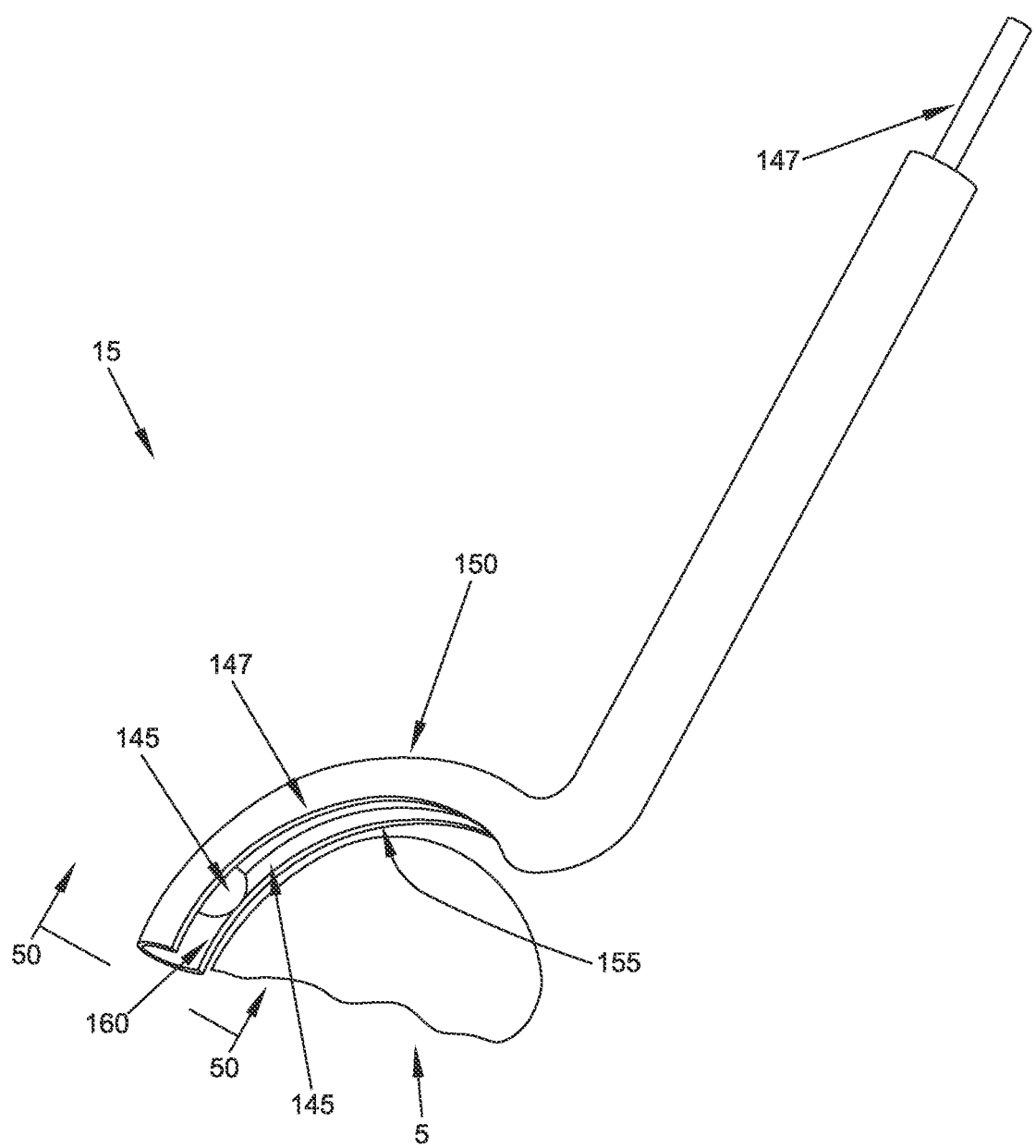
FIGS. 44-46 are schematic views of another arthroscopic debridement template formed in accordance with the present invention.
Figure 45:
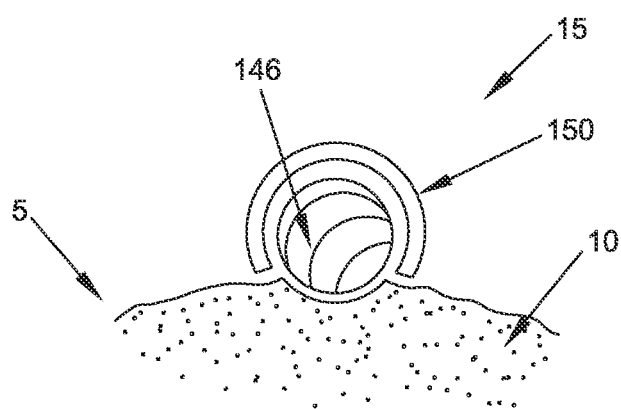
Figure 46:
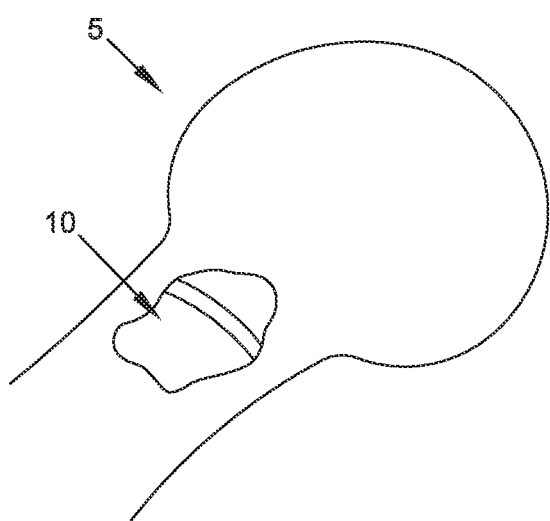

In another form of the present invention, and looking now at FIGS. 44-46, arthroscopic debridement template 15 incorporates a bone cutting element 145. More particularly, in this form of the invention, a bone cutting element 145 (e.g., a burr 146 turned by a torque coil 147) is housed within a sheath 150 which forms an arc 155 (FIG. 44). Arc 155 of sheath 150 has a configuration which matches the desired bone geometry. Sheath 150 comprises a slot 160 through which a portion of bone cutting element 145 extends (FIG. 45). To debride the bone, sheath 150 is placed on the target bone surface, then bone cutting element 145 (e.g., the burr) is moved along the arced sheath 150, removing bone in the process (FIG. 46). After bone cutting element 145 has completed its sweep along arced sheath 150, thereby forming a complete cut in the bone, sheath 150 is repositioned on the target bone and the bone removal process is repeated.

Use of the Novel Arthroscopic Debridement Template for Applications Other than the Treatment of Cam-Type Femoroacetabular Impingement It should be appreciated that the novel arthroscopic debridement template of the present invention may be used for applications other than the treatment of cam-type femoroacetabular impingement.

By way of example but not limitation, the novel arthroscopic debridement template of the present invention may be used to guide debridement of the acetabulum during treatment of pincer-type femoroacetabular impingement.

By way of further example but not limitation, the novel arthroscopic debridement template of the present invention may be used to guide debridement in joints other than the hip joint (e.g., to guide debridement of a surface of a humerus in order to prepare that surface for reattachment of a torn rotator cuff).

And by way of additional example but not limitation, the novel arthroscopic debridement template of the present invention may be used in non-arthroscopic procedures.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A method for debriding a bone, said method comprising:
   providing an apparatus comprising:
      an arthroscopic debridement template comprising at least two markers for disposition within the bone, wherein said at least two markers each comprise a body discernable from bone;
   identifying a bony protrusion on a bone to be debrided;
   implanting said at least two markers within the bone that is to be debrided, wherein said at least two markers are implanted at locations which demarcate at least one of (i) the perimeter of the bony protrusion which is to be removed from the bone to be debrided, and (ii) the depth of the amount of the bony protrusion which is to be removed from the bone to be debrided; and
   debriding the bony protrusion using said arthroscopic debridement template for guidance.

2. A method according to claim 1 wherein said at least two markers each comprise a rod.

3. A method according to claim 1 wherein said at least two markers are each formed out of a radiopaque material.

4. A method according to claim 1 wherein at least one of the at least two markers comprises a biocompatible material.

5. A method according to claim 1 wherein implanting said at least two markers comprises driving said at least two markers directly into the bone.

6. A method according to claim 1 wherein implanting said at least two markers comprises drilling at least two holes into the bone and inserting said at least two markers into the holes.

7. A method according to claim 1 wherein at least one of the at least two markers comprises surface features for enhancing engagement with the bone.

8. A method according to claim 1 wherein at least one of the at least two markers comprises plastic.

9. A method according to claim 1 wherein at least one of the at least two markers comprises stainless steel.

10. A method according to claim 1 wherein the bony protrusion is on an outer surface of the bone, wherein the at least two markers are implanted into the outer surface of the bone in a first direction, and further wherein the bony protrusion is debrided by approaching the bony protrusion from the first direction.

* * * * *